United States Patent
Paukshto et al.

(10) Patent No.: US 10,238,769 B2
(45) Date of Patent: Mar. 26, 2019

(54) GRAFT FOR DIRECTED VASCULAR AND LYMPHATIC REGENERATION AND METHODS TO GUIDE ENDOTHELIAL CELL ASSEMBLY

(71) Applicants: Fibralign Corporation, Union City, CA (US); The Board of Trustees of the Leland Stanford Junior University, Palo Alto, CA (US)

(72) Inventors: Michael V. Paukshto, Foster City, CA (US); John P. Cooke, Palo Alto, CA (US); Tatiana S. Zaitseva, San Jose, CA (US); Ngan F. Huang, Mountain View, CA (US); Gerald G. Fuller, Stanford, CA (US); George R. Martin, Rockville, MD (US)

(73) Assignees: Fibralign Corporation, Union City, CA (US); The Board of Trustees of the Leland Stanford Junior University, Stanford, CA (US)

( * ) Notice: Subject to any disclaimer, the term of this patent is extended or adjusted under 35 U.S.C. 154(b) by 527 days.

(21) Appl. No.: 14/351,128

(22) PCT Filed: Oct. 11, 2012

(86) PCT No.: PCT/US2012/059830
§ 371 (c)(1),
(2) Date: Apr. 10, 2014

(87) PCT Pub. No.: WO2013/103423
PCT Pub. Date: Jul. 11, 2013

(65) Prior Publication Data
US 2014/0242347 A1 Aug. 28, 2014

Related U.S. Application Data

(60) Provisional application No. 61/627,289, filed on Oct. 11, 2011.

(51) Int. Cl.
*A61L 27/24* (2006.01)
*A61L 27/36* (2006.01)
(Continued)

(52) U.S. Cl.
CPC .......... *A61L 27/24* (2013.01); *A61L 27/3604* (2013.01); *A61L 27/3808* (2013.01);
(Continued)

(58) Field of Classification Search
CPC .. A61F 2310/00371; A61F 2310/00982; A61F 2002/061; A61L 27/24
(Continued)

(56) References Cited

U.S. PATENT DOCUMENTS

| | | | | |
|---|---|---|---|---|
| 4,816,028 A | * | 3/1989 | Kapadia | ............... A61F 2/06 139/387 R |
| 5,171,273 A | | 12/1992 | Silver et al. | |

(Continued)

FOREIGN PATENT DOCUMENTS

| | | |
|---|---|---|
| WO | WO 99/047188 | 9/1999 |
| WO | WO 00/61045 A1 | 10/2000 |

(Continued)

OTHER PUBLICATIONS

Besseau, Laurence et al., "Stabilization of Fluid Cholesteric Phases of Collagen to Ordered Gelated Matrices", Journal of Molecular Biology, vol. 251, pp. 197-202, Aug. 1995.
(Continued)

*Primary Examiner* — Brian Pellegrino
(74) *Attorney, Agent, or Firm* — Nixon Peabody LLP

(57) ABSTRACT

Embodiments of the present invention relate to a therapeutic device (graft) comprising a collagen membrane having an aligned uniaxial or biaxial structure such that mammalian cells plated on the membrane align mainly along the direction of the collagen fibrils. In a further aspect, a graft
(Continued)

comprising a substantially tubular body, wherein the body has an exterior surface, an interior surface, and at least one lumen extending therethrough such that a fluid flow through the lumen can direct mammalian cell migration. In a further aspect, mammalian cells or growth and angiogenic factors can be optionally attached to the exterior and/or interior surface of the substantially tubular body. In various aspects, the graft can be used as a vascular prosthesis, a stent, or a nerve regeneration scaffold. Methods of preparing and implanting same are also provided.

21 Claims, 30 Drawing Sheets

(51) Int. Cl.
*A61L 27/38* (2006.01)
*A61L 27/50* (2006.01)

(52) U.S. Cl.
CPC ......... *A61L 27/507* (2013.01); *A61L 2430/32* (2013.01); *Y10T 428/24711* (2015.01); *Y10T 428/249921* (2015.04); *Y10T 428/26* (2015.01)

(58) Field of Classification Search
USPC ...................................................... 623/1.35
See application file for complete search history.

(56) References Cited

U.S. PATENT DOCUMENTS

| | | | |
|---|---|---|---|
| 5,378,469 A | | 1/1995 | Kemp et al. |
| 5,968,546 A | * | 10/1999 | Baur .................. A61L 27/3813 424/444 |
| 6,544,762 B1 | | 4/2003 | Tranquillo et al. |
| 6,592,623 B1 | | 7/2003 | Bowlin et al. |
| 6,887,488 B2 | | 5/2005 | Cui et al. |
| 7,048,963 B2 | | 5/2006 | Braithwaite et al. |
| 7,338,517 B2 | | 3/2008 | Yost et al. |
| 7,648,471 B2 | | 1/2010 | Hobson |
| 7,744,914 B2 | | 6/2010 | Li et al. |
| 8,028,647 B2 | | 10/2011 | McMurtry et al. |
| 8,227,574 B2 | | 7/2012 | Paukshto et al. |
| 8,513,382 B2 | | 8/2013 | Paukshto et al. |
| 9,724,308 B2 | | 8/2017 | Paukshto et al. |
| 2002/0090725 A1 | * | 7/2002 | Simpson ................ A61L 27/24 435/402 |
| 2003/0093107 A1 | | 5/2003 | Parsonage et al. |
| 2006/0085063 A1 | | 4/2006 | Shastri et al. |
| 2006/0198827 A1 | | 9/2006 | Levenberg |
| 2006/0228339 A1 | | 10/2006 | Wang |
| 2007/0041952 A1 | | 2/2007 | Guilak et al. |
| 2008/0147199 A1 | | 6/2008 | Yost et al. |
| 2009/0069893 A1 | | 3/2009 | Paukshto et al. |
| 2009/0104159 A1 | | 4/2009 | Prosper et al. |
| 2009/0280180 A1 | * | 11/2009 | Voytik-Harbin ........ A61L 27/24 424/484 |
| 2010/0021520 A1 | * | 1/2010 | Baskin .................. A61L 27/24 424/423 |
| 2010/0036098 A1 | | 2/2010 | Paukshto et al. |
| 2011/0151563 A1 | | 6/2011 | Paukshto et al. |
| 2011/0206646 A1 | | 8/2011 | Alfonso et al. |
| 2012/0065703 A1 | | 3/2012 | Paukshto et al. |
| 2012/0125348 A1 | | 5/2012 | Alitalo et al. |
| 2013/0287744 A1 | | 10/2013 | Paukshto et al. |
| 2014/0081070 A1 | | 3/2014 | Paukshto et al. |
| 2016/0256605 A1 | | 9/2016 | Hadamitzky et al. |

FOREIGN PATENT DOCUMENTS

| | | |
|---|---|---|
| WO | WO 2003/020316 A1 | 3/2003 |
| WO | WO 2004/050134 A2 | 6/2004 |
| WO | WO 2005/003300 A2 | 1/2005 |
| WO | WO 2005/081699 A2 | 9/2005 |
| WO | WO 2006/136817 A1 | 12/2006 |
| WO | WO 2007/028078 A2 | 3/2007 |
| WO | WO 2007/038601 A2 | 4/2007 |
| WO | WO 2008/034854 A1 | 3/2008 |
| WO | 2008/063631 A2 | 5/2008 |
| WO | WO 2008/070166 A1 | 6/2008 |
| WO | WO 2008/131293 A2 | 10/2008 |
| WO | WO 2009/064437 A1 | 5/2009 |
| WO | 2011/028579 A2 | 3/2011 |
| WO | WO 2012/034110 A2 | 3/2012 |
| WO | WO 2013/103423 A2 | 7/2013 |
| WO | WO 2014/018685 A1 | 1/2014 |
| WO | WO 2015/054654 A1 | 4/2015 |

OTHER PUBLICATIONS

Gobeaux, F. et al., "Fibrillogenesis in Dense Collagen Solutions: A Physicochemical Study", Journal of Molecular Biology, vol. 376, pp. 1509-1522; Mar. 2008.
Hulmes, David J.S., "Building Collagen Molecules, Fibrils; and Suprafibrillar Structures", Journal of Structural Biology, vol. 137, pp. 2-10, Jan. 2002.
Kirkwood, John E. et al., "Liquid Crystalline Collagen: A Self-Assembled Morphology for the Orientation of Mammalian Cells", Langmuir, 2009, vol. 25, pp. 3200-3206, published on web Feb. 10, 2009.
Lai, Edwina S. et al., "Aligned nanofibrillar collagen regulates endothelial organization and migration", Regenerative Medicine, vol. 7, No. 5, pp. 649-661, 2012.
International Search Report and Written Opinion in International Application No. PCT/US2012/059830, dated Jul. 25, 2013.
Besseau, L. et al., "Production of Ordered Collagen Matrices for Three-Dimensional Cell Culture," Biomaterials, 23, 2002, pp. 27-36.
Boardman et al., "Interstitial Flow as a Guide for Lymphangiogenesis", Circulation Research, vol. 92, No. 7, pp. 801-808, published online Mar. 2003.
Cisneros, D. et al., "Creating Ultrathin Nanoscopic Collagen Matrices for Biological and Biotechnological Applications", Wiley InterScience, 2007, vol. 3, No. 6, pp. 956-963.
Eglin, D. et al., "Type I Collagen, a Versatile Liquid Crystal Biological Template for Silica Structuration from Nano-to Microscopic Scales," The Royal Society of Chemistry, vol. 1, 2005, pp. 129-131.
Evans, H., et al. "Novel 3D Culture System for Study of Cardiac Myocyte Development," Am J. Physiol Heart Circ Physiol, vol. 285, 2003, pp. H570-H578.
Freed, A.D. et al., "Elastic Model for Crimped Collagen Fibril," Journal of Biomechanical Engineering, Aug. 2005, vol. 127, pp. 587-593.
Gobeaux, F., "Cooperative Ordering of Collagen Triple Helices in the Dense State", Langmuir 2007, vol. 23, pp. 6411-6417.
Guo, C, et al., "Flow and Magnetic Field Induced Collagen Alignment," Biomaterials, vol. 28, 2007, pp. 1105-1114.
Hibino et al., "A Critical Role for Macrophages in Neovessel Formation and the Development of Stenosis in Tissue-Engineered Vascular Grafts", The FASEB Jounal, Dec. 2011 (published online Aug. 2011), vol. 25, No. 12, pp. 4253-4263.
Huang et al., "The Modulation of Endothelial Cell Morphology, Function, and Survival Using Anisotropic Nanofibrillar Collagen Scaffolds", Biomaterials, May 2013 (published online Mar. 2013), vol. 34, No. 16, pp. 4038-4047.
Jiang, et al., Assembly of collagen into microribbons: effects of pH and electrolytes; Journal of Structural Biology, Academic Press, United States, vol. 148, No. 3, Dec. 1, 2004; pp. 268-278.
Knight, D. et al. "Biological Liquid Crystal Elastomers," Philosophical Transactions: Biological Sciences, vol. 357, No. 1418, Estomeric Proteins: Structures, Biomechanical Properties and Biological Roles, Feb. 12, 2002, pp. 155-163.
Koster, et al., Visualization of Flow-Aligned Type I Collagen Self-Assembly in Tunable pH Gradients; Langmuir, vol. 23, 2007, pp. 357-359.

(56) References Cited

OTHER PUBLICATIONS

Ledet, E. H. et al., "A Pilot Study to Evaluate the Effectiveness of Small Intestinal Submucosa Used to Repair Spinal Ligaments in the Goat," The Spine Journal, vol. 2, No. 3, May-Jun. 2002, pp. 188-196.
Martin, G. R. et al., "Behavior of Cells on Highly Organized and Reconstituted Collagen Matices," The Cell, Bethesda MS USA, vol. 19, Dec. 13, 2008, p. 42.
Martin, R. et al., "Liquid Crystalline Ordering of Procollagen as a Determinant of Three-Dimensional Extracellular Matrix Architecture," J. Mol. Biol., vol. 301, 2000, 11-17.
Mosser, G., et al., "Dense tissue-like collagen matrices formed in cell-free conditions", Matrix Biology, 2006, 25, pp. 3-13.
Muthusubramaniam, L. et al., "Collagen Fibril Diameter and Alignment Promote the Quiescent Keratocyte Phenotype", J Biomed Mater Res Part A, 100A, (3), 613-621, published online Dec. 2011.
Yan et al., "Mechanisms of Lymphatic Regeneration After Tissue Transfer", PLoS One, vol. 6, No. 2, e17201, pp. 1-12, Feb. 2011.
Yoshizato, K. et al., "In Vitro Orientation of Fibroblasts and Myoblasts on Aligned Collagen Film", Develop., Growth and Differ., 23 (2), 1981, pp. 175-184.
Zhong, S. et al., "An Aligned Nanofibrous Collagen Scaffold by Electrospinning and its Effects on In Vitro Fibroblast Culture", Journal of Biomedical Materials Research Part A, 2006 Wiley Periodicals, Inc., pp. 456-463.
International Search Report and Written Opinion in International Application No. PCT/US2014/060164, dated Mar. 12, 2015.
Office Action in U.S. Appl. No. 15/028,391, dated Nov. 20, 2017.
Office Action in U.S. Appl. No. 15/028,391, dated Mar. 22, 2018.

\* cited by examiner

FIG. 6A. Align-braided

FIG. 6B. Tendon-like

FIG 6C. Basket-Weave

FIG. 6D. Cornea-like

GRAFT FOR DIRECTED VASCULAR AND LYMPHATIC REGENERATION AND METHODS TO GUIDE ENDOTHELIAL CELL ASSEMBLY

CROSS REFERENCE TO RELATED APPLICATIONS

This patent application is a United States National Stage Application filed under 35 U.S.C. § 371 of International Application No. PCT/US2012/059830, entitled "A Graft For Directed Vascular And Lymphatic Regeneration And Methods To Guide Endothelial Cell Assembly" which was filed on Oct. 11, 2012 which claims the benefit of, and priority to, U.S. Provisional Patent application Ser. No. 61/627,289, filed on Oct. 11, 2011, entitled "Device and Methods to Guide Endotheial Cell Assembly" the entire disclosure of which is hereby incorporated by reference.

GOVERNMENT RIGHTS

This application was partially supported by the US Army Medical Research and Materiel Command under Contract No. W81XWH-12-C-0111.

FIELD

Embodiments of the present invention relate generally to a therapeutic device (graft) comprising a collagen membrane having an aligned uniaxial or biaxial structure such that mammalian cells plated on the membrane align mainly along the direction of the collagen fibrils.

BACKGROUND

Cardiovascular disease is the major cause of morbidity and mortality in the USA. Most cardiovascular disease is attributable to the effects of atherosclerosis, with myocardial infarction and stroke due to atherosclerotic plaque rupture, thrombosis and/or embolism. Notably, the distribution of atherosclerotic lesions in the blood vessels is not uniform. Lesions tend to form at sites of disturbed flow (e.g., bends, branches and bifurcations). At these sites, there is an early disturbance of normal endothelial functions, which represents the earliest pathological process in the development of atherosclerotic arterial disease.

The endothelium is a delicate monolayer of cells lining blood vessels. A healthy endothelium controls vessel diameter by producing vasodilator substances. Some of these substances, such as nitric oxide and prostacyclin, also inhibit the adhesion of platelets and leukocytes. These and other paracrine substances released by the endothelium prevent vascular thrombosis and inflammation. By contrast, at sites of disturbed flow, the endothelium produces fewer homeostatic factors, and instead elaborates adhesion molecules and chemokines that promote the interaction of circulating blood elements with the vessel wall.

The morphology of endothelial cells (ECs) is a well-known indicator of EC phenotype. Elongated ECs with cytoskeletal elements aligned in the direction of blood flow correspond to a healthy, atheroresistant phenotype. This endothelial morphology is typically observed in straight segments of the arterial tree, where atherosclerotic lesions are less likely to develop. By contrast, ECs with cobblestone morphology and randomly oriented EC cytoskeletons are typically found at sites of disturbed flow, and are atherosusceptible. After vascular injury or disease, EC migration is important in the angiogenesis process to form neovessels in the surrounding tissue. EC migration involves protrusion of filopodia and lamellipodia at the leading edge, forward movement of the cell body and release of the lagging edge of the cell. Therefore, the ability to control EC morphology and motility, with the aim to influence EC biology, might be highly beneficial in the prevention or treatment of vascular disease. Surfaces of patterned topography, with features in the micrometer or nanometer-scale range, have been widely used to investigate the behavior of cells. Nanopatterning, in the form of islands, lanes or grooves, has successfully demonstrated the ability to influence both the morphology and migration of ECs. See Anderson D, Hinds M., Endothelial Cell Micropatterning: Methods, Effects, and Applications, *Ann. Biomed. Eng.* 39, 2329-2345 (2011); Lauffenburger D A, Horwitz A F., Cell Migration: A Physically Integrated Molecular Process. *Cell* 84, 359-369 (1996); Li S, Bhatia S, Hu Y L et al., Effects of Morphological Patterning on Endothelial Cell Migration, *Biorheology* 38, 101-108 (2001); Liliensiek S J, Wood J A, Young J, Auerbach R, Nealey P F, Murphy C J, Modulation of Human Vascular Endothelial Cell Behaviors by Nanotopographic Cues, *Biomaterials* 31(20), 5418-5426 (2010); Junkin M, Wong P K, Probing Cell Migration in Confined Environments by Plasma Lithography, *Biomaterials* 32(7), 1848-1855 (2011); Uttayarat P, Chen M, Li M, Allen F D, Composto R J, Lelkes P I, Microtopography and Flow Modulate the Direction of Endothelial Cell Migration, *Am. J. Physiol. Heart Circ. Physiol.*, 294(2), H1027-H1035 (2008); Zorlutuna P, Rong Z, Vadgama P, Hasirci V. Influence of Nanopatterns on Endothelial Cell Adhesion: Enhanced Cell Retention Under Shear Stress, *Acta Biomater.*, 5, 2451-2459 (2009); and Slater J H, Frey W. Nanopatterning of Fibronectin and the Influence of Integrin Clustering on Endothelial Cell Spreading and Proliferation, *J. Biomed. Mater. Res. A,* 87(1), 176-195 (2008). Commonly used fabrication techniques include soft lithography, photochemistry, inkjet printing or electrospinning. These techniques, however, may have limitations in achieving high-resolution features, reproducibility, translation to 3D surfaces or need expensive fabrication requirements such as described in Anderson D, Hinds M. Endothelial Cell Micropatterning: Methods, Effects, and Applications, *Ann. Biomed. Eng.*, 39, 2329-2345 (2011).

The aligned collagen matrices used here can be made according to the patent applications "Biocomposites and Method of Making the Same" U.S. patent application Ser. No. 12/539,563, (2009), and "Oriented Collagen-Based Materials, Films and Methods of Making Same" World Intellectual Property Organization 2008, WO/2008/131293, the disclosures of which are hereby incorporated by reference in their entirety.

Additionally, the references to Lai E., Huang N., Cooke J., Fuller G. Aligned Nanofibrillar Collagen Regulates Endothelial Organization and Migration, *Regen. Med.* 7(5), 649-661 (2012); J. E. Kirkwood, G. G Fuller. Liquid Crystalline Collagen: A Self-Assembled Morphology for the Orientation of Mammalian Cells, Langmuir, 25, (5), 3200-3206 (2009), and Lai E., Huang N., Cooke J., Fuller G. Aligned Nanofibrillar Collagen Regulates Endothelial Organization and Migration. Regen., *Med.* 7(5), 649-661 (2012) are cited herein, or by the method described in the FIG. 13, which is a generalization of the coating method and device described in "Liquid Film Applicator Assembly and Rectilinear Shearing System Incorporating the Same", World Intellectual Property Organization 2008, WO/2008/063631 to a cylindrical geometry, the entire disclosure of which is hereby incorporated by reference. These matrices can form planar membranes, cylindrical tubular membranes, or general 3D membranes. The membranes can have single or multiple layers with arbitrary orientation of collagen fibrils in each layer. Unlike previous patterning methods used to regulate the cytoskeletal organization of ECs, the aligned collagen matrices do not use physical or biochemical confinement to restrict the cell motion, thereby better mimicking native extracellular matrices (ECMs). The aligned collagen matrices also provide a useful platform to investigate EC migration, where previous migration investigations have been limited to conditions using hemodynamic shear, chemotactic gradients or physical channels.

The typical structures/devices to direct endothelial cell alignment and migration use the groove-like topography like shown in the FIG. 2 and oriented fiber/fibril topography which is similar to the groove-like topography, see FIG. 3 and FIG. 4. The main mechanism of the endothelial cell alignment/orientation on such substrates is the constraints induced by the fibers/fibrils and groove's walls (substrate "contact guidance"). This is consistent with the observation that the "surface feature depth" is "shown to induce greater alignment response on feature depths more than 300 nm" as in Abrams, G. A.; Teixeira, A. I.; Nealey, P. F.; Murphy, C. J., Effects of Substratum Topography on Cell Behavior. In Biomimetic Materials and Design: Biointerfacial Strategies, Tissue Engineering and Targeted Drug Delivery; Dillow, A. K., Lowman, A. M., Eds.; CRC Press: New York, N.Y., USA, 2002; pp. 91-137; and Brody, S.; Anilkumar, T.; Liliensiek, S.; Last, J. A.; Murphy, C. J.; Pandit, A., Characterizing Nanoscale Topography of the Aortic Heart Valve Basement Membrane for Tissue Engineering Heart Valve Scaffold Design, *Tissue Eng.*, 2006, 12, 413-421.

The aligned collagen matrices produced according to disclosures found in Biocomposites and Method of Making the Same, U.S. patent application Ser. No. 12/539,563, (2009), and Oriented Collagen-Based Materials, Films and Methods of Making Same, World Intellectual Property Organization 2008, WO/2008/131293 have quite different surface topography, see also L. Muthusubramaniam, L. Peng, T. Zaitseva, M. Paukshto, G. R. Martin, T. A. Desai, Collagen Fibril Diameter and Alignment Promote the Quiescent Keratocyte Phenotype *J Biomed Mater Res A,* 100A, (3), 613-621 (2012). The typical example is presented in the FIG. 5. This is a dense fibrillar collagen matrix which is formed by crimped fibrils oriented in one direction. The crimped configurations of collagen fibrils are typical for collagen-based fibrous tissue when external load is reduced, and mimic the woven spiral structure of collagen bundles in relaxed blood vessels, see K. P Arkill, J. Moger, C. P. J. Winlove, The Structure and Mechanical Properties of Collecting Lymphatic Vessels: an Investigation Using Multimodal Nonlinear Microscopy, *Anat.* 216, (5), 547-55 (2010). The grooves in the FIG. 5 are oriented perpendicular to the fibril direction. Fibroblasts, smooth muscle cells, and endothelial cells plated on this matrix are aligned and migrate along the fibril direction which is perpendicular to the grooves and crimp ridges.

Threads/sutures/fibers made from type I collagen solution have been researched extensively as scaffolds for repair and regeneration and recently for cell delivery applications, see D. Enea, F. Henson, S. Kew, J. Wardale, A. Getgood, et al., Extruded Collagen Fibres for Tissue Engineering Applications: Effect of Crosslinking Method on Mechanical and Biological Properties, *J. Mater Sci: Mater Med.* 22, 1569-1578 (2011); K G Cornwell, P Lei, S T Andreadis, G D Pins, Crosslinking of Discrete Self-Assembled Collagen Threads Effects on Mechanical Strength and Cell-Matrix Interactions., *J. Biomed Mater Res A.* 80A, 362-71 (2007); and D I Zeugolis, G R Paul, G. Attenburrow, Cross-linking of Extruded Collagen Fibers a Biomimetic Three-dimensional Scaffold for Tissue Engineering Applications, *J. Biomed Mater Res A.* 89A, 895-908 (2009). One of the first commercial extruded collagen sutures was manufactured by Ethicon, see A. Smith, Extruded Collagen Ophthalmic Sutures. A clinical survey, *Brit. J. Ophthal.*, 54, 522-527 (1970). Organogenesis, see P. D. Kemp, R M Karr, J G Maresh, J. Cavallaro, J. Gross, Collagen threads, U.S. Pat. No. 5,378,469, (1995) further improved the extrusion process. Since this time the principal parts of the procedure remain the same and the extruded thread/suture/fiber has a shape of a long compact cylinder with near circular cross-section. "The success of these scaffolds has been limited by insufficient tissue ingrowth from the wound margin", see K G Cornwell, P Lei, S T Andreadis, G D Pins, Crosslinking of Discrete Self-assembled Collagen Threads: Effects on Mechanical Strength and Cell-matrix Interactions., *J. Biomed Mater Res A.* 80A, 362-71 (2007), because of the collagen high density and crosslinking treatment used to increase the mechanical properties and decrease the degradation rate of these scaffolds.

The novel thread-like collagen construct (scaffold) as described in U.S. patent application Ser. No. 12/539,563, (2009), the entire disclosure of which is hereby incorporated by reference, produced from thin (1-2 um) collagen ribbon has a completely different structure, see FIG. 16 and FIG. 7. It consists of highly aligned collagen fibrils and has a large surface area suitable for cell ingrowth, see FIG. 1.

Purified collagen from animal or human sources is widely used in various medical devices, in research, and in cosmetics. However, the materials prepared from soluble purified collagen lack the diversity in macrostructure and organization observed in tissues. For example, the collagen fibers in tendon are highly aligned for maximal tensile strength, but also have a kinked structure to allow for tissue flexibility. In contrast, the collagen in the cornea is arranged as small parallel transparent fibers. The collagen in the skin is arranged in bundles, not parallel, which allows more expansion and flexibility than seen with tendon. Each structure provides obvious advantages to the tissue it comprises.

Collagen prepared from both human and animal sources has been shown to be safe and of minimal immunogenicity when implanted into humans. Collagen has the advantages that it is biocompatible, can form structures with high tensile strength, that the tensile strength of the constructs can be increased by covalent cross-linking and that the construct is replaced by normal tissue by repair and regeneration.

Methods to deposit collagen molecules in defined structures including aligned, woven and transparent materials for diverse indications are described in U.S. patent application Ser. Nos. 11/951,324, 11/986,263, 12/106,214, and 12/539,563 and paper Lai E., Huang N., Cooke J., Fuller G. Aligned Nanofibrillar Collagen Regulates Endothelial Organization and Migration, Regen., *Med.* 7(5), 649-661, (2012), all of which are incorporated by reference herein in their entirety. One advantage of these collagen materials is that they closely approximate the natural structures of tissues, are biocompatible and induce the guided growth of cells attached to them. The collagen materials appear to be an excellent substrate for applying endothelial cells to precise tissue sites. While these advances have been made, there is significant need for continued advancement and development of devices, constructs, implants and methods that promote and/or enhance tissue repair and regeneration, particularly constructs for vascular and lymphatic engineering.

SUMMARY

Embodiments of the present invention relate to a therapeutic device (graft) comprising a collagen membrane having an aligned uniaxial or biaxial structure such that mammalian cells plated on the membrane align mainly along the direction of the collagen fibrils. In a further aspect, a graft comprising a substantially tubular body, wherein the body has an exterior surface, an interior surface, and at least one lumen extending therethrough such that a fluid flow through the lumen can direct mammalian cell migration. In a further aspect, mammalian cells or growth and angiogenic factors can be optionally attached to the exterior and/or interior surface of the substantially tubular body. In various aspects, the graft can be used as a vascular prosthesis, a stent, or a nerve regeneration scaffold. Methods of preparing and implanting same are also provided.

In some embodiments, a graft is provided comprising a collagen membrane comprising collagen fibrils and having an aligned uniaxial or biaxial structure such that mammalian cells plated on the membrane align mainly along the direction of the collagen fibrils. In some embodiments, the graft comprises a collagen membrane having an aligned-crimped structure such that mammalian cells plated on the membrane align substantially perpendicular to the ridges and grooves of the crimp pattern and primarily along the direction of the crimped fibrils. In some embodiments, the membrane exhibits a transmission diffraction pattern produced by a laser source with wavelength in the visible range, such that the pattern has at least two centrally symmetric elongated "petals". The cells may be endothelial cells and their alignment degree depends on the diameter of the collagen fibrils forming the membrane.

In some embodiments the majority of collagen fibrils have a diameter in a range from 20 nm to 60 nm. When the cells are endothelial cells they may be aligned mainly along the direction of the collagen fibrils.

In another embodiment, a graft is provided wherein the membrane is rolled and folded in a thread-like construct, wherein the construct is further cross-linked and has viscoelastic properties under uniaxial load. In some embodiments, the thread-like construct has at least one cavity elongated substantially along the construct suitable for carrying cells, growth factors, drugs, other suitable bioactive materials and cell formations like endothelial spheroids and islets. In some embodiments, the thread-like construct has a multi-luminal nodular compartment suitable for embedding such cells like thymus derived stromal cells and bone marrow derived dendritic cells to generate a lymph node-like immune response function, and the flanking thread-like sections with no or single lumen suitable to carry and align endothelial cells to integrate the lymph node prosthesis into lymphatic system and link it to the blood circulation. In other embodiments, the thread-like construct has multi-luminal structure with crimped fibrils align along its partial or substantial length and multiple lumens within the construct running parallel with the construct length. In some embodiments the one or more of the multiple lumens start and stop at (or are segmented along) various locations or places along the construct.

Of particular advantage the construct exhibits desirable tensile strength. For example, in some embodiments the construct has a diameter in the range from about 50 μm to about 2 mm in a dry state, and tensile strength is higher than 0.2 MPa in the wet state. Additionally, the construct may exhibit Fung-elastic material properties after precondition to a load pattern with a first constant A ranging from about 0.2 MPa to about 300 MPa and a second constant B ranging from about 0.5 MPa to about 200 MPa when measured in the wet state.

Of further advantage, in some embodiments the construct promotes angiogenesis, vascularization and provides a means for guiding migration and orientation of endothelial cells as well as the cell localization.

In another embodiment, a graft is provided comprising a substantially tubular body, wherein the body has an exterior surface, an interior surface, and at least one lumen extending therethrough such that an fluid flow through the lumen can direct endothelial cell migration. In a further aspect, mammalian cells or growth and angiogenic factors can be optionally attached to the exterior and/or interior surface of the substantially tubular body. In various aspects, the graft can be used as a vascular prosthesis, a stent, or a nerve regeneration scaffold and can be delivered in a mammalian subject by catheter, trocar, or other minimally invasive procedure.

In other embodiments, a construct is provided that promotes directed vascular or lymphatic regeneration. In some embodiments, the membrane guides endothelial cell assembly and diminishes the pathological adherence of circulating blood elements causing inflammation or thrombosis. In other embodiments the membrane guides endothelial cell assembly and extends the survival of cells in ischemic tissue. The membrane may be formed of at least one or more type of collagens: I, II, III, IV, V, VI or XI.

In other embodiments at least one thread-like construct is attached to a carrier with lymph node or lymph node fragment or mammalian decellularized lymph node and prepared for transferring or transplanting a graft in a mammalian subject by catheter, trocar, or other minimally invasive procedure, wherein the construct promotes survival of the lymph node and integration of the lymph node into a lymphatic network in the mammalian subject, at the site of transfer or transplantation.

In another aspect, a graft is provided comprising a multilayer collagen membrane with the top layer having an aligned-crimped structure and the bottom layer having aligned-crimped structure such that the alignment directions of the top and bottom layers form an angle, wherein the mammalian cells plated on the membrane align substantially perpendicular to the ridges and grooves of the crimp pattern and substantially along the direction of the crimped fibrils in each layer. In some embodiments the exterior surface has aligned-crimped structure and the interior surface has aligned-crimped structure such that the alignment directions of the exterior and interior surfaces form an angle. The angle may be a 90° angle and the alignment direction of the crimped fibrils of the interior surface coincides with the direction of at least one lumen.

The grant may further comprises growth factors, peptides, elastin, fibrin, heparin, proteoglycans, glycoproteins, hyaluronan, cross-linking agents, or combinations thereof. The cells may be selected from the group consisting of myocyte precursor cells, smooth muscle cells, cardiac myocytes, skeletal myocytes, satellite cells, fibroblasts, cardiac fibroblasts, chondrocytes, osteoblasts, osteocytes, endothelial cells, epithelial cells, epidermal cells, embryonic stem cells, hemopoietic cells, neuronal cells, Schwann cells, mesenchymal stem cells, glial cells, dorsal root ganglia, anchorage-dependent cell precursors, or combinations thereof.

The inventors have found that fibroblasts and smooth muscle cell alignment is less sensitive to the thickness of the collagen fibrils while endothelial cells align better on thin fibrils, see FIG. 27. Thus the alignment mechanism on the aligned collagen matrix used here is different than the typical "contact guidance" mechanism described above.

The device and process to align endothelial cells according to some embodiments of the present invention depends in part on the diameter of the collagen fibrils. Possible variations could include binding endothelial growth factors such as VEGF, VEGF-C, VEGF-D, or small molecules (drugs, mRNA, antibodies) that can enhance endothelial proliferation, maintain endothelial differentiation, and/or attract circulating endothelial progenitor cells. The finding that this material and device induces endothelial cell alignment has many opportunities for commercialization, several of which are presented below, for illustration only and without limitation.

Bypass graft. Endothelial cells at sites of anastamoses with bypass grafts are generally not aligned and express receptors, which can promote the adhesion of lipogenic proteins or monocytes and thus lead to occlusions within the graft. By restricting the alignment of endothelial cells using fibrillar collagen matrix, the endothelial cells may be less prone to monocyte adhesion and may have improved patency.

Implantable device. Endothelial cells implanted to induce/stimulate/improve angiogenesis at the sites of compromised circulation, when delivered in a suspension format, usually do not survive long enough to exert any beneficial effects. Delivery of endothelial cells on fibrillar collagen graft improves their survival and may improve their angiogenic potential.

Bilayered graft. Endothelial cells lining the interior wall of blood vessel are aligned along the vessel, while the smooth muscle cells comprising the outer layer of the vessel are aligned at 90° to the vessel axis. A bilayered graft with interior layer having the fibril alignment along the vessel axis, and the outer layer having the fibril alignment perpendicular to that of the inner layer will provide guidance for endothelial cells to align inside the graft along its axis and for the smooth muscle cells on the outer surface of the graft to align perpendicular to the vessel axis. Aligning both endothelial and muscle layers according to their natural topography may improve patency of the graft. This model of the vessel may also be used for in-vitro studies (e.g. drug discovery, device testing, etc.).

The device comprises collagen membranes manufactured from solutions of clinical grade monomeric collagen having a specific liquid crystal phase and deposited on glass or plastic using a liquid film applicator assembly which provides optimal conditions for the self-assembly of collagen molecules into aligned, aligned-crimped, and aligned-braided fibrils. The resulting fibrillar material has regularly sized aligned fibrils, crimps, periodicity, and angular distribution. Using the parallel-aligned fibrillar collagen matrix, endothelial cells are grown on top and through the porous matrix, where the cellular orientation is controlled by the collagen fibrillar matrix orientation. In addition to orienting the endothelial cells morphologically, the aligned fibrillar collagen matrix also beneficially affects endothelial cell function.

Whereas it is well established that physiological levels of laminar shear stress induced by fluid flow can orient endothelial cells along the direction of shear stress, promote nitric oxide production, and inhibit monocyte adhesion, this invention demonstrates that matrix-induced cellular alignment can mimic some of the same beneficial vasoprotective properties as cellular alignment induced by physiological levels of laminar shear stress.

The device and the process of orienting endothelial cells on the graft mimic the effect of shear-induced cellular alignment in their ability to control cell morphology as well as cell function. In particular, endothelial cell F-actin filaments and focal adhesion plaques orient along the direction of collagen fibrils, and the parallel-aligned endothelial cells attract fewer monocytes in contrast to randomly oriented endothelial cells.

BRIEF DESCRIPTION OF THE FIGURES

The foregoing and other aspects of embodiments of the present disclosure will be apparent upon consideration of the following detailed description, conjunct the accompanying drawings, in which like reference characters refer to like parts throughout, and in which:

FIGS. 26A-26D show two-photon intravital microscopy depicting FITC-dextran infusion into the systemic circulation at 5 weeks after subcutaneous transplantation of genipin-crosslinked graft (thread-like construct) and subsequent histological analysis of the graft (FIGS. 26A, 26B). The genipin-crosslinked collagen graft is depicted; with arrows indicating direction of nanofibrils of the scaffold. FIG. 26C shows H&E staining of collagen graft (arrow) at low and high magnification showing the presence of endogenous cells.

FIG. 27B is FD100-MP-membrane with fibril diameter about 100 nm and additional sinusoidal profile microgrooves with 10 micron period and about 300 nm depth in the direction of the fibrils, FIG. 27C shows FD100-membrane with fibril diameter about 100 nm, and FIG. 27D is FD30-membrane with fibril diameter about 30 nm. SEM images shown in FIG. 27E of control and in FIG. 27F of FD30 membranes. Arrows denote direction of collagen fibrils. FIG. 27G represents quantification of mean cell alignment, with respect to nanofibril direction. In this analysis, a value of 45° represents entirely random orientation of axes of cultured cells. In FIG. 27H cell alignment was also quantified by two-dimensional FFT analysis and is depicted by alignment plots. Insets represent corresponding frequency plots. The sign (*) indicates statistically significant difference for comparison with control at day 4 (P<0.0001); # indicates statistically significant difference for comparison with control at day 7. Scale bars: 50 µm (A-G), 100 µm (I-J).

(FIG. 28A)—fluorescent images of U937 monocytes adhered onto ECs grown on control or FD30 membrane substrates (FIG. 28B)—Quantification of relative fold change in monocyte adhesion. Scale bar, 100 µm. * indicates significant difference (p<0.001).

In FIG. 29C Immunofluorescence staining for endothelial marker CD31 and nuclei is shown; In FIG. 29D. Immunofluorescence staining for cell cycle marker, Ki67 and nuclei is shown. Arrow denotes direction of collagen nanofibrils. Scale bar: 200 µm (A), 10 µm (B), 50 µm (C-D).

In FIG. 30A, BLI reveals cell localization and survival of ECs when delivered in DMEM (C) or on the FD30 scaffold (C+S), in comparison to FD30 scaffold (S) alone. In FIG. 30B, Quantification of bioluminescence intensity is illustrated. Dotted line indicates threshold for positive signal.

In FIG. 31A, BLI reveals cell localization and survival of ECs when delivered in PBS (C) or on the FD30 nanofibrillar scaffold (C+S). In FIG. 31B, Quantification of bioluminescence intensity is shown. Dotted line indicates threshold for positive signal.

DETAILED DESCRIPTION

It is to be understood that both the foregoing general description and the following description are exemplary and explanatory only and are not restrictive of the methods and devices described herein. In this application, the use of the singular includes the plural unless specifically state otherwise. Also, the use of "or" means "and/or" unless stated otherwise. Similarly, "comprise," "comprises," "comprising," "include," "includes," "including," "has," "have," and "having" are not intended to be limiting.

The examples of the embodiments are described herein in the context of medical graft and biocompatible constructs, and methods of making but other applications are possible. Those of ordinary skill in the art will realize that the follsdyowing description is illustrative only and is not intended to be in any way limiting. Other embodiments will readily suggest themselves to such skilled persons having the benefit of this disclosure. Reference will now be made in detail to various implementations of the example embodiments as illustrated in the accompanying drawings. The same reference indicators will be used to the extent possible throughout the drawings and the following description to refer to the same or like items.

Various embodiments of the grafts of the present invention are also sometimes referred to as scaffolds, collagen scaffolds, membranes, implants and/or bio-devices. The terms biocompatible polymer and biopolymer are sometimes used interchangeably. The terms layer(s) and membrane(s) are sometimes used interchangeably.

Figure 5:
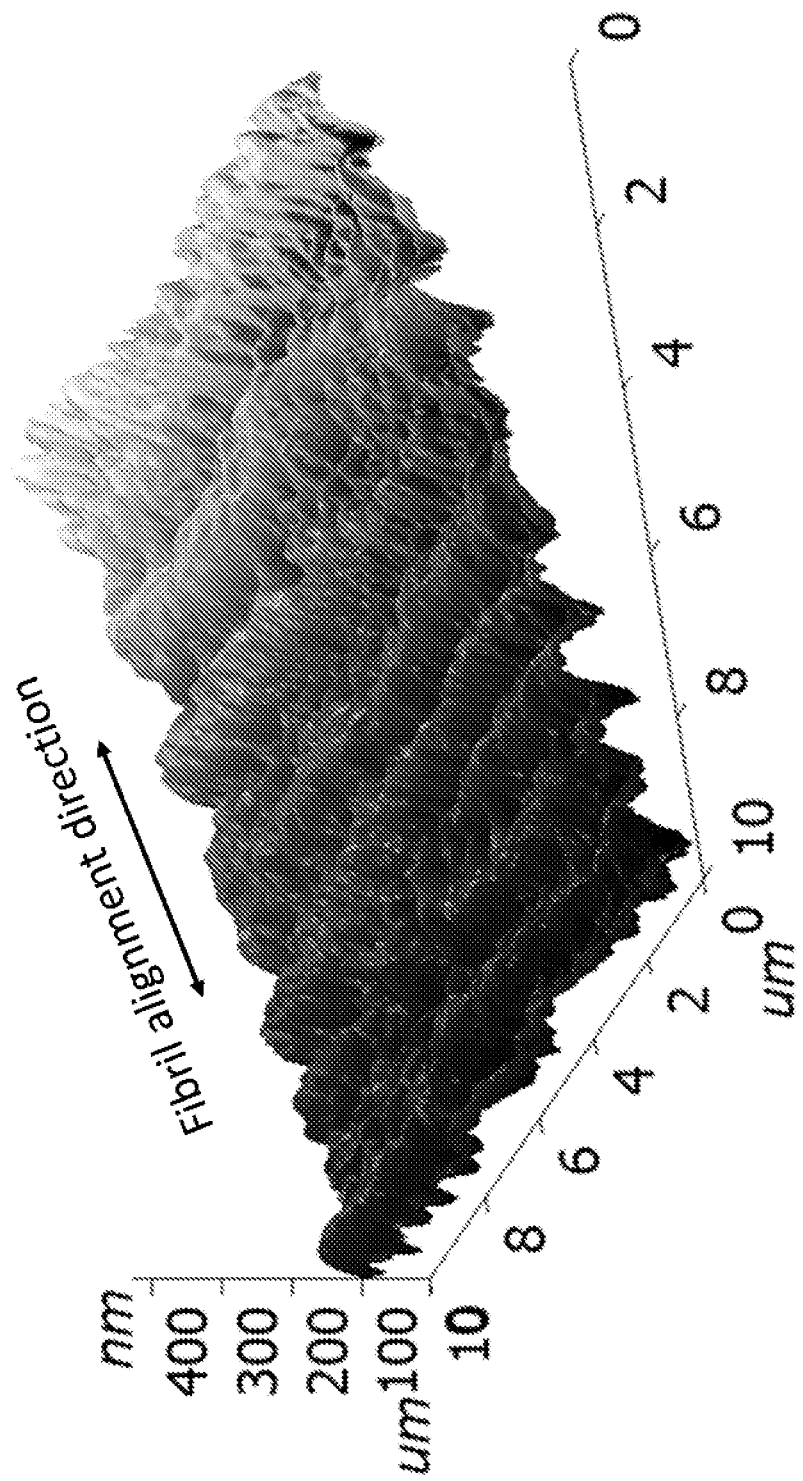
FIG. 5 shows the 3D-surface topography of collagen aligned-crimped matrix. The grooves and ridges formed by crimped collagen fibrils are aligned perpendicular to the fibrils. Human microvascular and lymphatic endothelial cells align perpendicular to the grooves but along to the fibril direction. The aligned-crimped matrices can be deposited on the substrate or they can be used as free-standing matrices.
Figure 6:
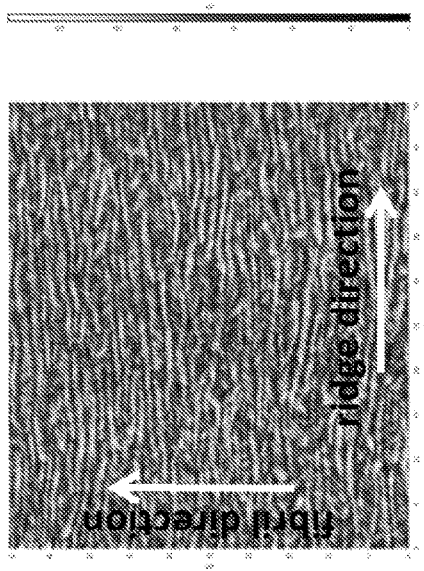
FIGS. 6A-6D present the AFM measurements of collagen membranes made according to the patent applications Biocomposites and Method of Making the Same, U.S. patent application Ser. No. 12/539,563, (2009); and Oriented Collagen-based Materials, Films and Methods of Making Same., World Intellectual Property Organization 2008, WO/2008/131293. The membranes in FIG. 6A, FIG. 6B, and FIG. 6D have aligned uniaxial structure; the membrane in FIG. 6C has aligned biaxial structure. The membranes in FIG. 6A, FIG. 6B, and FIG. 6C are made from medical grade atelocollagen type I; membrane in the FIG. 6D is made from collagen type III. It is very important that different endothelial cells should be guided by different membranes. For example, microvascular endothelial cells does not align on the membrane presented in the FIG. 6A but perfectly align on the membrane presented in the FIG. 6B. Therefore the fibril alignment is not enough for the cell guidance.
Figure 6:
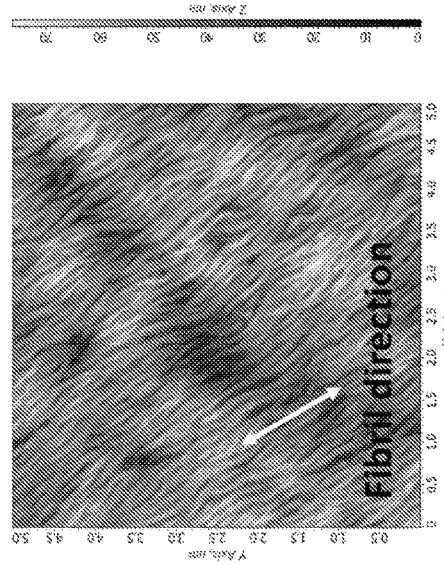
Figure 6:
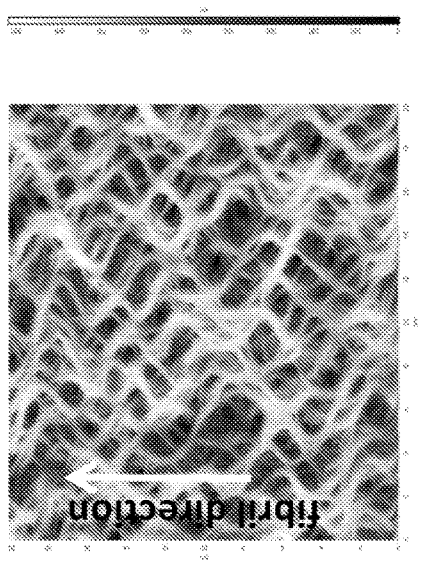
Figure 6:
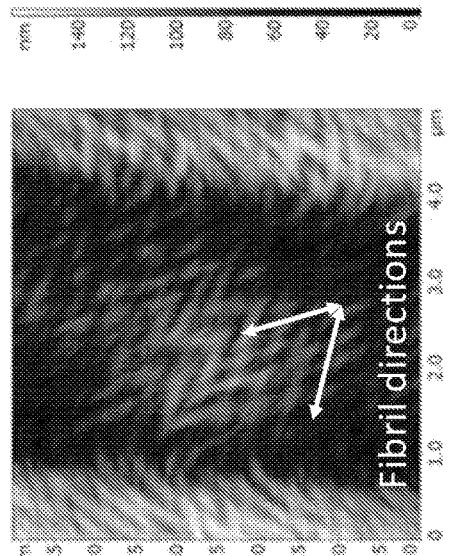
Figure 14:
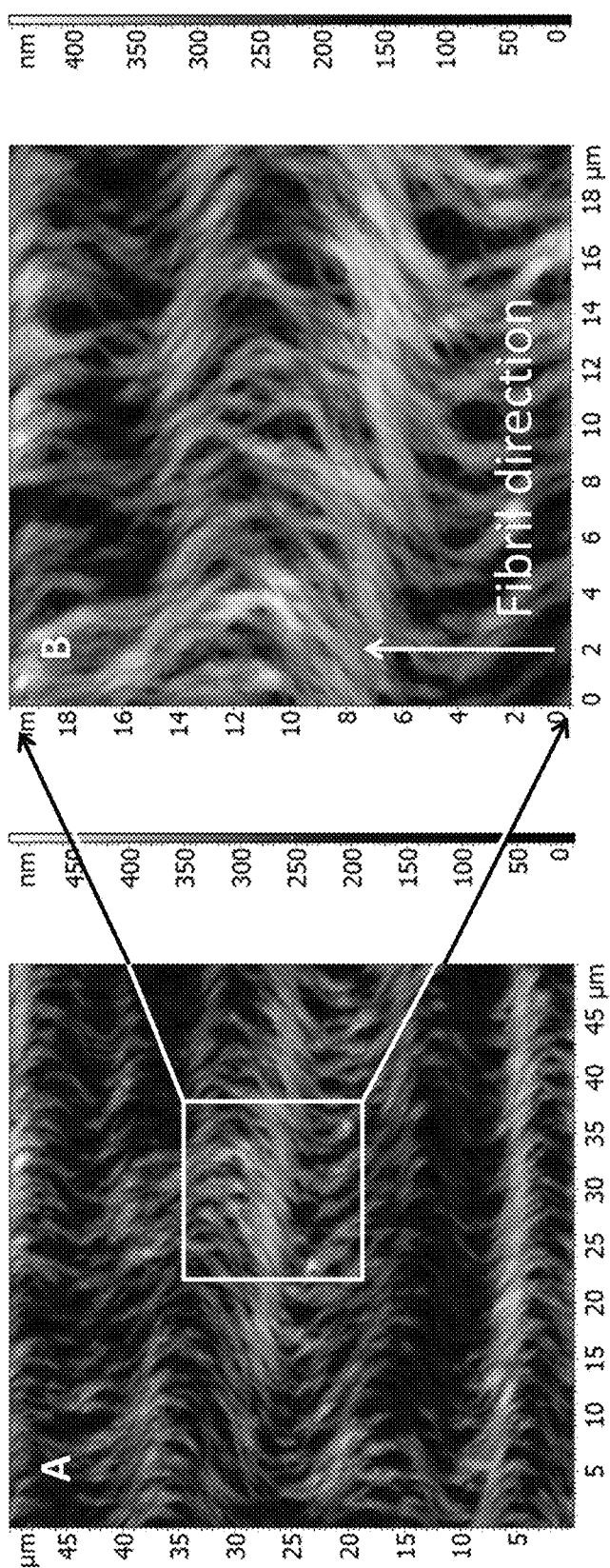
FIGS. 14A and 14B present the AFM photograph of the aligned-crimped collagen membrane. One can see the crimped collagen fibrils forming parallel ridges and groves which are perpendicular to the fibril direction.

As used herein the term "collagen membrane" always means "fibrillar collagen membrane", where the typical fibrils or fibril bundles have elongated (rode-like) crimped structure (helical or deformed helical structure) in the unloaded state. Therefore it is natural to define the fibril orientation and the structure of the collagen membranes with respect to the oriented fibrillar structural elements. Such structural properties like, for example, uniaxial or biaxial structures are widely used in the disclosure. The "collagen membrane" or "nanoweave collagen membrane" means a fibrillar biopolymer membrane or layer where the filling fibrils or fibril bundles pass under and over alternate warp fibrils or fibril bundles, and the typical fibrils or fibril bundles have a helical or crimp shape in the unloaded state. Examples of various fibrillar nanoweave collagen membranes are shown in FIG. 14, FIGS. 5-6. Specifically, FIGS. 6A-6D show four distinct nanoweave collagen membranes reconstituted from purified monomeric collagen solution in accordance with U.S. patent application Ser. Nos. 11/951,324, 11/986,263, 12/106,214, and 12/539,563 and used in embodiments of the present disclosure.

Other materials that can produce fibrillar nanoweave membrane are fibrin, laminin, fibronectin, silk, and other lyotropic liquid crystal biopolymers.

The diameter of fibrils can be of any suitable size. In some embodiments, the diameter of the fibrils ranges from 20 nm to 500 nm, depending on the tissue requirement. Methods of making these highly organized fibrillar biopolymer membranes or layers are described in U.S. patent application Ser. Nos. 11/951,324, 11/986,263, 12/106,214, and 12/539,563, the disclosures of all of which are incorporated by reference herein in their entirety.

In some embodiments the biopolymer constructs are multi-layered. Multi-layered constructs may be made from fibrillar nanoweave biopolymer membranes or layers which may exhibit different structural characteristics, such structural characteristics being selected in order to promote regeneration in the wounded tissue and block further cell migration in the direction of surrounding tissues. For example, the construct may be formed by several cross-linked collagen layers configured such that in the vicinity of the wounded tissue one or more of the collagen layers have selected porosity, enzymatic degradation, crosslinking, and mechanical properties that promote repair and regeneration, while the outer collagen layers (or collagen layers remote from the wounded tissue) are designed to ensure the mechanical strength of the whole construct.

Additionally, one or more of the outer collagen layers may exhibit selected properties that promote suturability of the construct, and/or provide a barrier to prevent cell migration though the construct during the time required for the tissue to repair and regenerate. In some embodiments a fibrillar nanoweave layer has uniaxial or unidirectional orientation of the fibrils (e.g., tendon-like or cornea-like membrane). In some cases a fibrillar nanoweave layer has biaxial orientation of the fibrils (e.g., basket-weave membrane) over all, or a portion of, the layer. Different forms or collagen may be used. In some embodiments, monomeric collagen is used. One example of monomeric collagen is monomeric collagen I with cleaved telopeptides or atellocollagen which has low immunogenicity.

Figure 4:
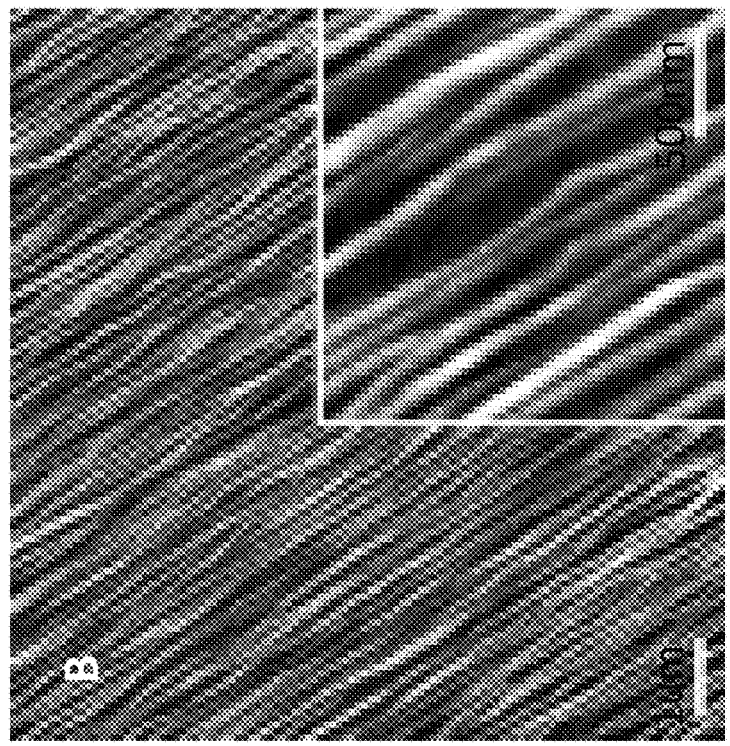
FIGS. 4A and 4B show low density aligned collagen coatings on substrate which form a groove-like surface topography. The substrate on the left is used to align bovine aortic endothelial cells (Leem P., et al., Microfluidic Alignment of Collagen Fibers for In Vitro Cell Culture, *Biomed Microdevices*, 8 (2006) 35-41). The substrate on the right is used to align human corneal endothelial cells (Gruschwitz et al, Alignment and Cell-Matrix Interactions of Human Corneal Endothelial Cells on Nanostructured Collagen Type I Matrices, *Investigative Ophthalmology & Visual Science*, 51:12, (2010) 6303-6310).
Figure 4:
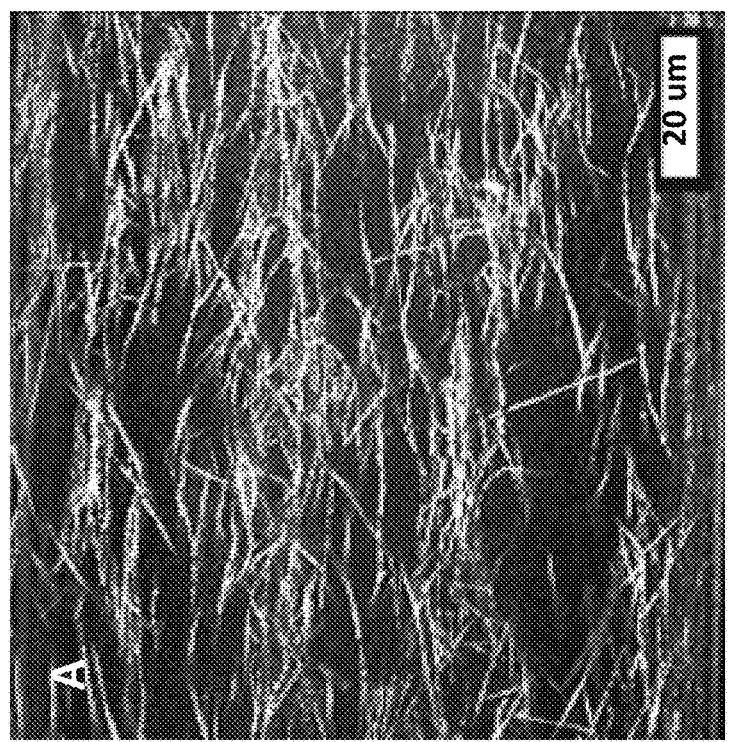
Figure 15:
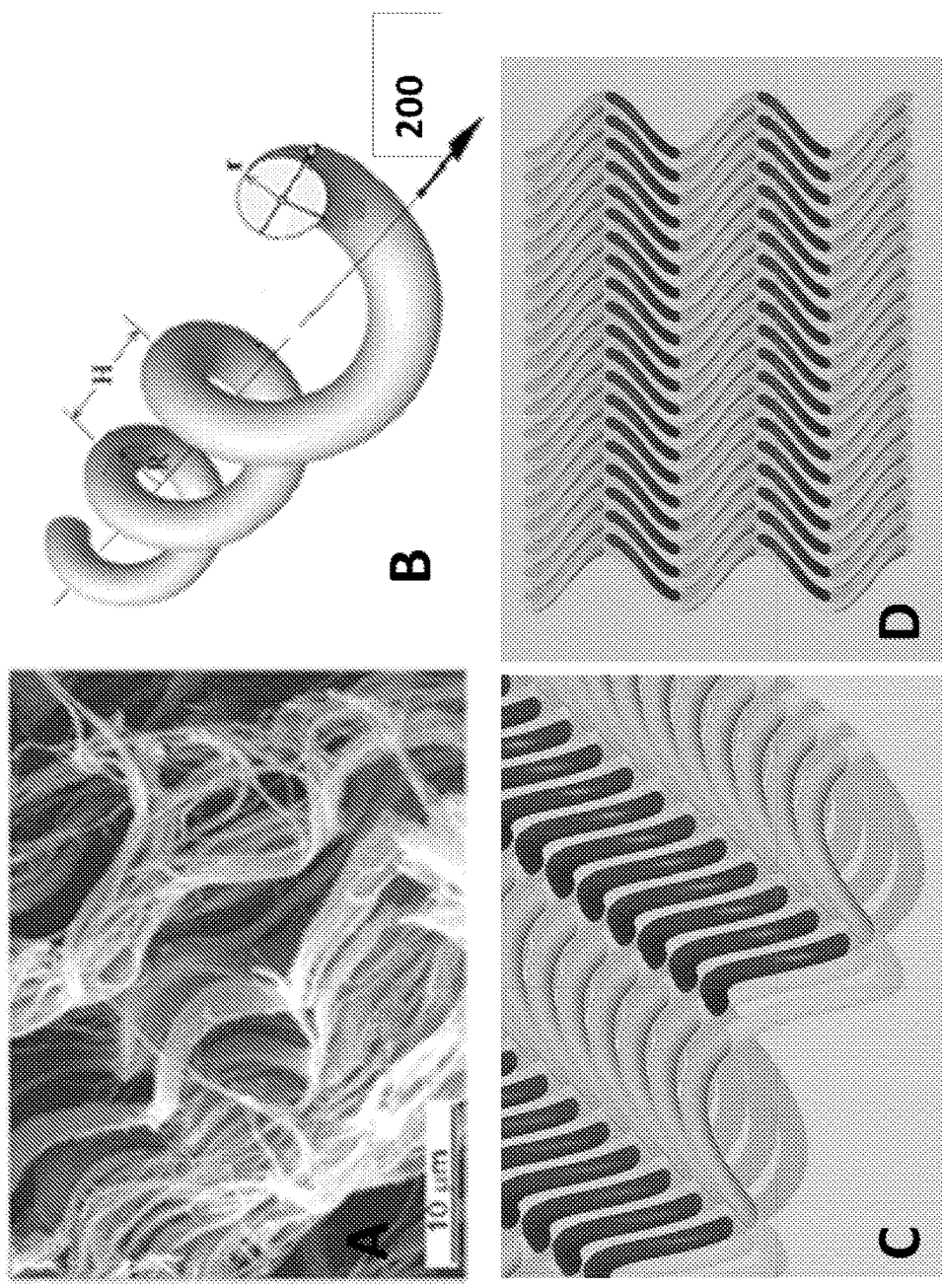
FIGS. 15A-15D show: SEM photograph (A) presenting the crimped structure of collagen fibrils in chordæ tendinæ taken from a porcine mitral valve; a schematic diagram (B) of the crimped fibril, where 200 is the fibril direction; a schematic diagrams (C, D) of the "crimp pattern", grooves, and ridges in the aligned-crimped membrane.

It is understood that fibrillar nanoweave collagen layer may influence non-scarring cell phenotype via mechanotransduction. The thread-like graft fabrication process is based on technology described in the patent application Biocomposites and method of making the same, U.S. patent application Ser. No. 12/539,563, (2009); and oriented collagen-based materials, films and methods of making same. World Intellectual Property Organization 2008, WO/2008/131293. and is suitable for lyotropic liquid crystal materials. Purified monomeric collagen (type I or III or other type) solution is concentrated according to previously published protocolssee Oriented collagen-based materials, films and methods of making same. World Intellectual Property Organization 2008, WO/2008/131293', and J. E. Kirkwood, G. G Fuller. Liquid Crystalline Collagen: A Self-Assembled Morphology for the Orientation of Mammalian Cells, Langmuir, 25, (5), 3200-3206 (2009). to reach a liquid crystal state and sheared onto plastic with optical precision using a liquid film applicator assembly, see Liquid film applicator assembly and rectilinear shearing system incorporating the same. World Intellectual Property Organization 2008, WO/2008/063631. The method enables control of fibril size, pitch, and helix diameter, as well as membrane thickness. Fibril diameter and alignment are varied by changing pH, ionic strength, collagen concentration, and ambient humidity (with the typical osmolarity ranging from 10 to 200 mOsm/Kg H2O). The membrane thickness is controlled by the gap in the coating head as described more fully in Liquid film applicator assembly and rectilinear shearing system incorporating the same, World Intellectual Property Organization 2008, WO/2008/063631 and fully incorporated herein by reference, and typically ranges from 1 to 5 μm. This membrane has aligned uniaxial or biaxial structure (see FIG. 6) and can be supported by substrate or can be removed from the substrate in the dry state as a free-standing membrane having anisotropic viscoelastic properties even before cross-linking, such that it has low but nonezero strength in the direction perpendicular to fibril direction and sufficiently high strength along the fibril direction. In contrast, the low density collagen layers in the FIG. 4 does not form membranes because they have zero strength in the direction perpendicular to the fibril direction and cannot be removed from substrate as one continued and stable layer. This example explains how we use the term "membrane" in the patent application. We understand here that "aligned uniaxial structure" is the structure with "uniaxial orientation" in the sense of the patent application Oriented collagen-based materials, films and methods of making same. World Intellectual Property Organization 2008, WO/2008/131293. The "biaxial structure" means the structure with two preferred orientations of fibrils. The "aligned-crimped structure" means "aligned uniaxial structure" with one preferred orientations of fibrils and crimp formations (of the "crimp pattern") perpendicular to the oriented crimped fibrils, see the FIG. 14, FIG. 15, and FIG. 5 for further explanation of the "crimp pattern", ridges (crimp formations), crimp fibrils, direction of the crimp fibril, and the 3D surface of aligned-crimped structure.

Figure 1:
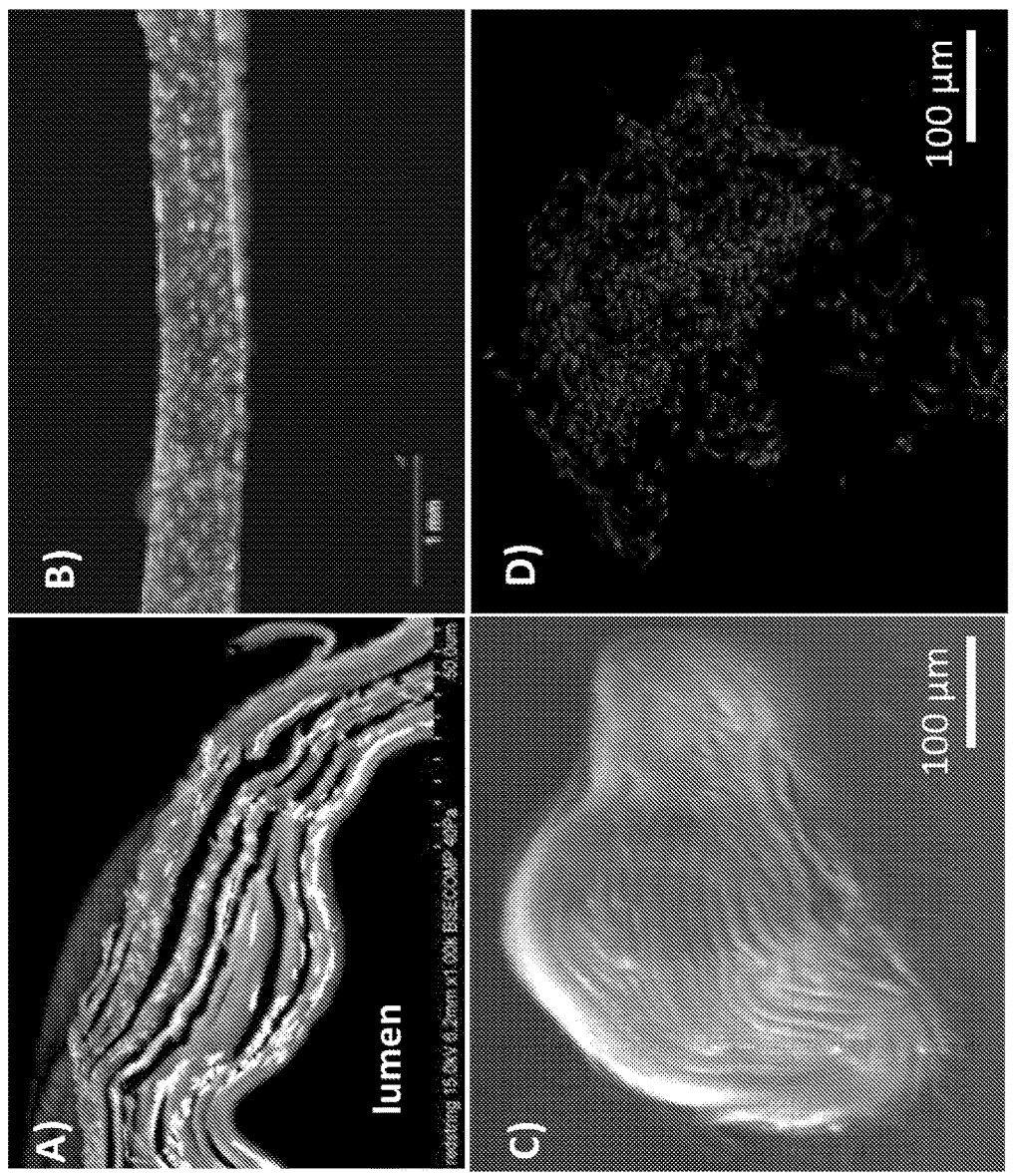
FIG. 1A is SEM image of the thread-like construct cross-section.
FIG. 1B shows Confluent hMECs on the thread-like construct, magnification 4×.
FIG. 1C shows Confocal image of the thread-like cross-section.
FIG. 1D shows Confocal image of hASC populated thread-like construct internal cavities (day 3 in culture).
Figure 2:
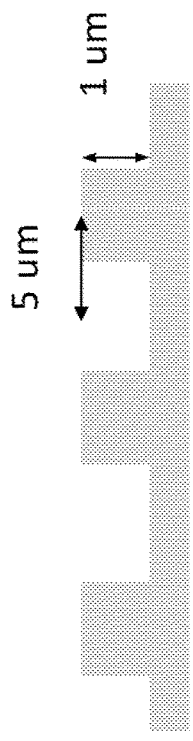
FIG. 2 presents the cross-section of micro-groove surface topography used to align endothelial cells (P. Uttayarat et al., *Acta Biomaterialia* 6, (2010) 4229-4237).
Figure 3:
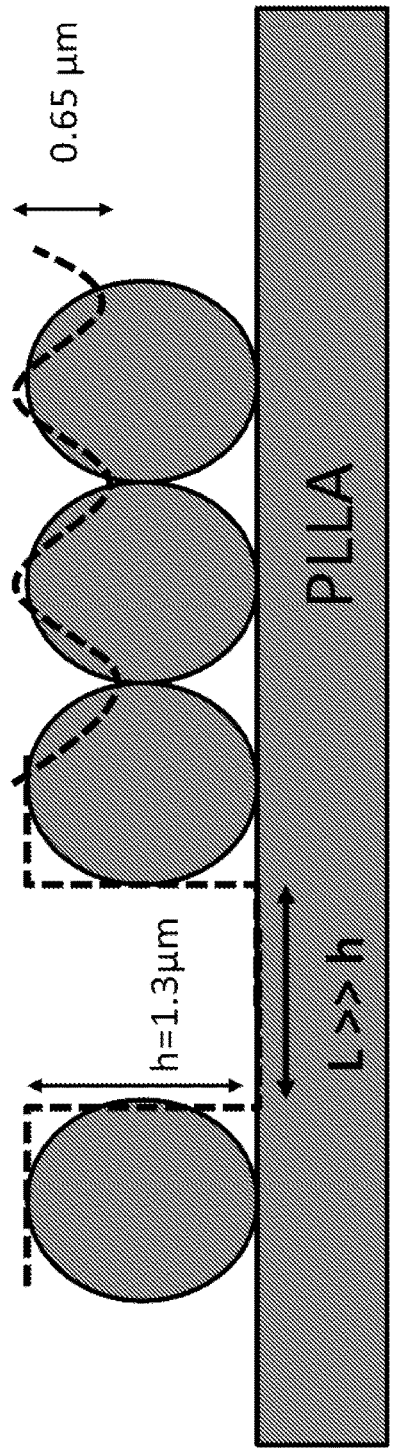
FIG. 3 represents the cross-section of groove-like surface topography used to align endothelial cells (Bouta E M, et al., Biomaterial Guides for Lymphatic Endothelial Cell Alignment and Migration, *Acta Biomaterialia* 7, (2011) 1104-1113).
Figure 16:
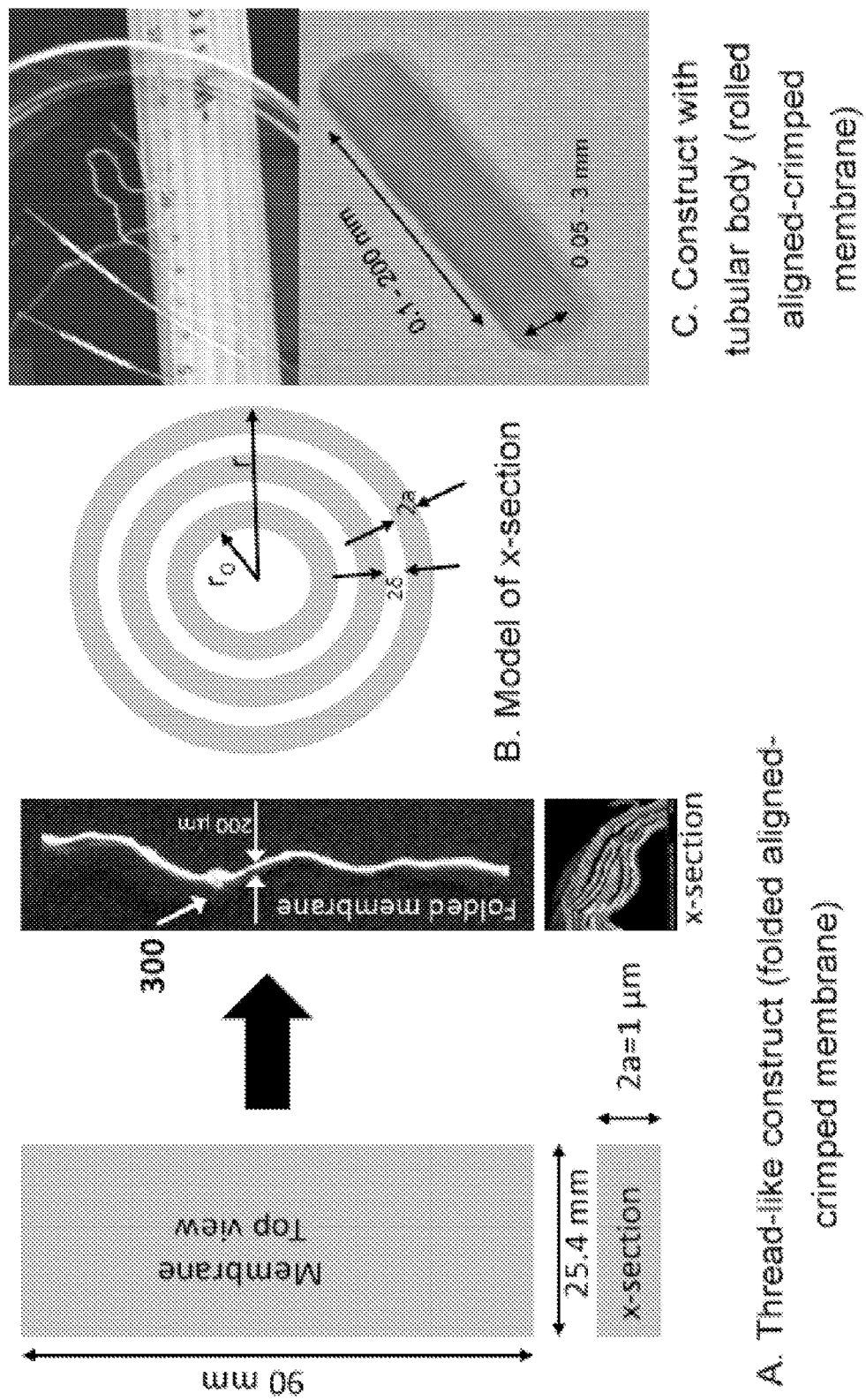
FIGS. 16A-16B show: transition from a ribbon-like membrane to a folded membrane—thread-like construct in FIG. 16A with nodular compartment 300; a model of thread-like cross-section in FIG. 16B, and; rolled membranes—the constructs with tubular bodies shown in FIG. 16C.

Thread-like collagen constructs (e.g., 10 mm long and 0.2 mm in diameters) for in vivo implantation are fabricated by shearing the liquid crystal collagen solution onto a plastic substrate, delaminating the resulting aligned-crimped membrane from the plastic, and converting the free-standing membrane into the scaffold using a liquid-air surface tension, see Biocomposites and method of making the same, U.S. patent application Ser. No. 12/539,563, (2009). Conversion of the free-standing membrane (1×25000 μm cross-section in dry state) into a thread (about 200 μm diameter) essentially consists in folding this membrane crosswise, and the resulting thread has multiple interconnected cavities (see FIG. 16, FIG. 7) which provide a space for cell attachment and migration (see FIG. 1). The interconnected cavities may serve as channels for interstitial fluid flow and lymphatic endothelial cell migration after an implantation into mammal body. Thus, the multi-luminal thread-like scaffold may represent an important device to help guide growth and organization of a developing lymphatic capillary network.

Several types of nanoweave collagen membrane can be made according to the methods described in the patent applications Biocomposites and method of making the same, U.S. patent application Ser. No. 12/539,563, (2009); and Oriented collagen-based materials, films and methods of making same. World Intellectual Property Organization 2008, WO/2008/131293, the disclosures of which have fully incorporated by reference herein.

They have been characterized by AFM Ntegra Prima and Solver Next (NT-MDT, Santa Clara, Calif.). The images in FIG. 6 have been acquired in the semi-contact mode using silicon tips NSG01 with typical radius <10 nm and spring constant 5.1 N/m (K-Tek Nanotechnology, Wilsonville, Oreg., USA).

Figure 7:
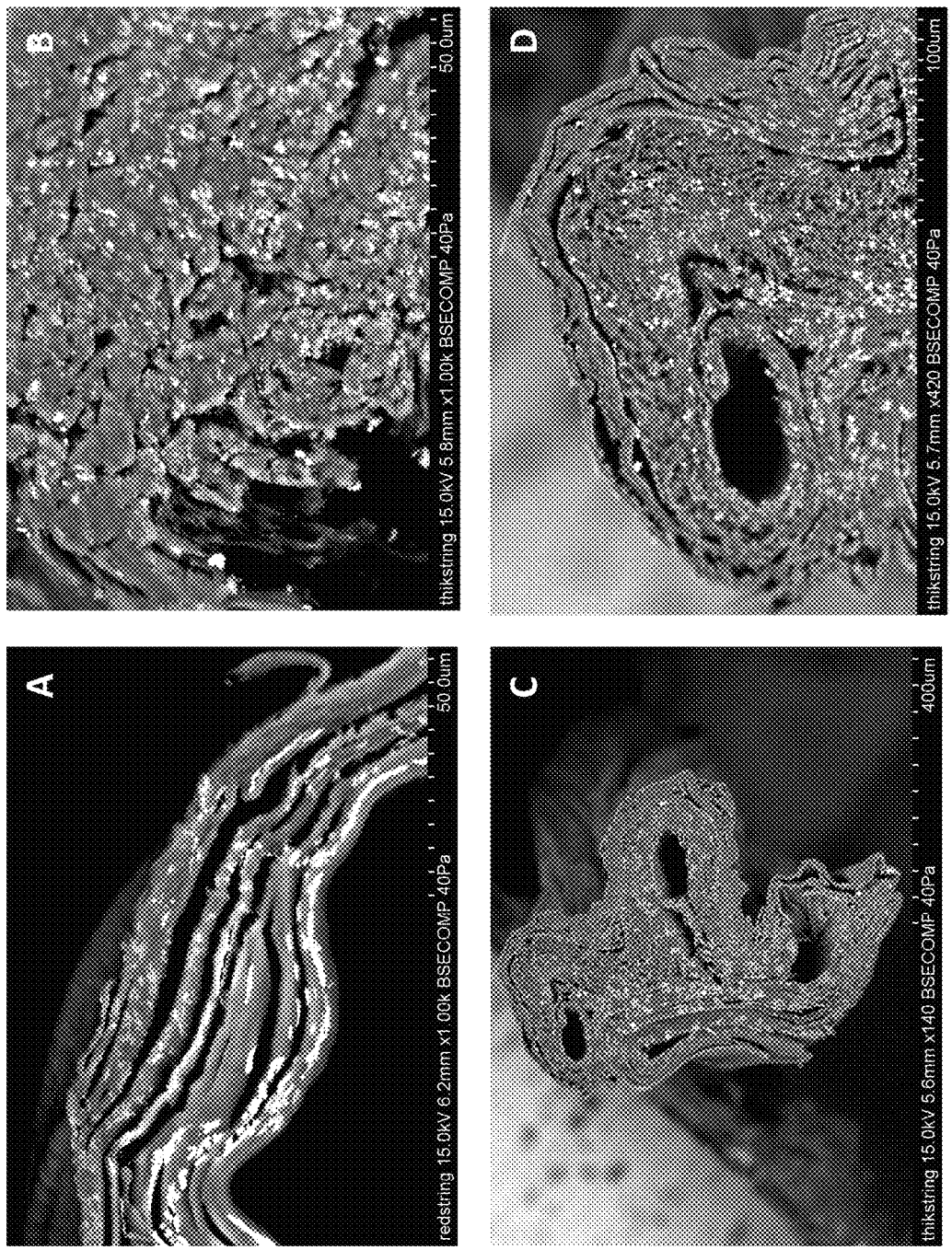
FIGS. 7A-7D show SEM measurement of thread-like construct cross-sections in the environmental (low vacuum) mode. Here the membranes in FIG. 7A and FIG. 7D have substantially tubular bodies with one lumen extending therethrough the thread-like construct. The thread-like construct in FIG. 7B has multiple elongated cavities and the construct in FIG. 7C has three lumens extending therethrough the thread.
Figure 8:
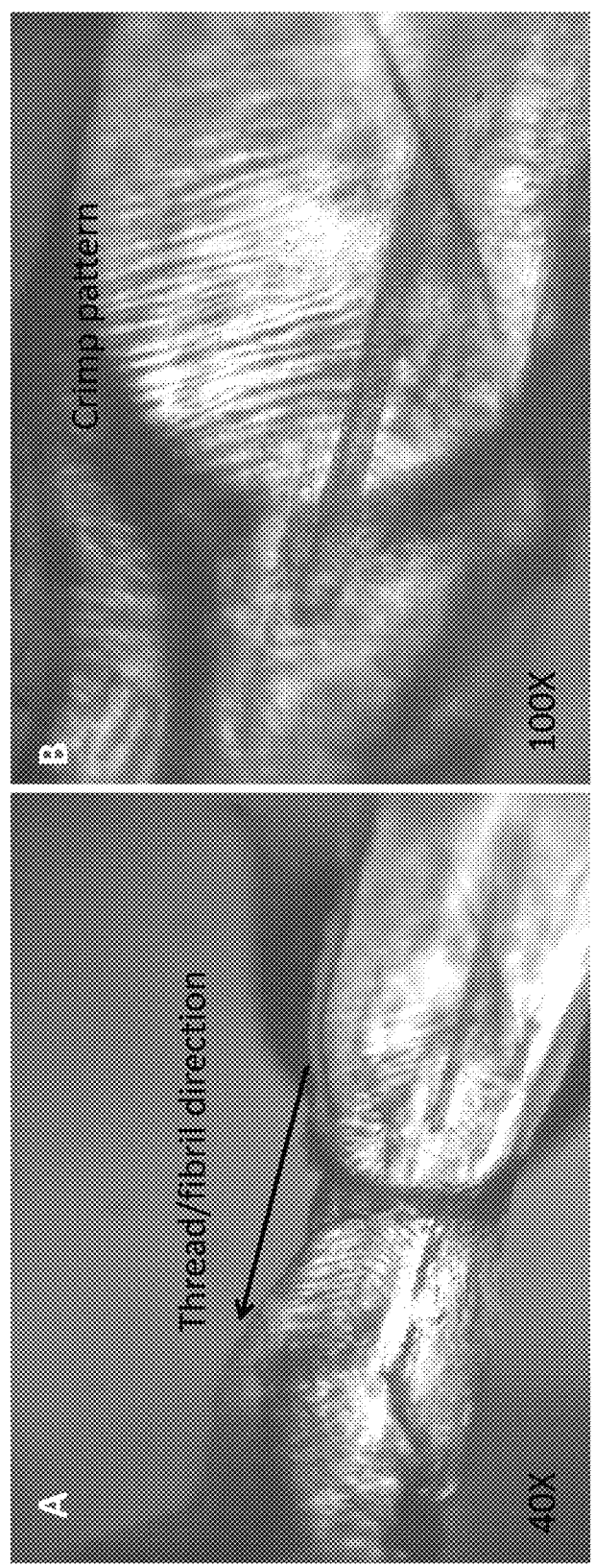
FIGS. 8A and 8B show a thread-like graft two weeks after implantation into mammal subject. Picture is made by polarized microscope such that the crimp structure is visible due to the variation in retardation.
Figure 9:
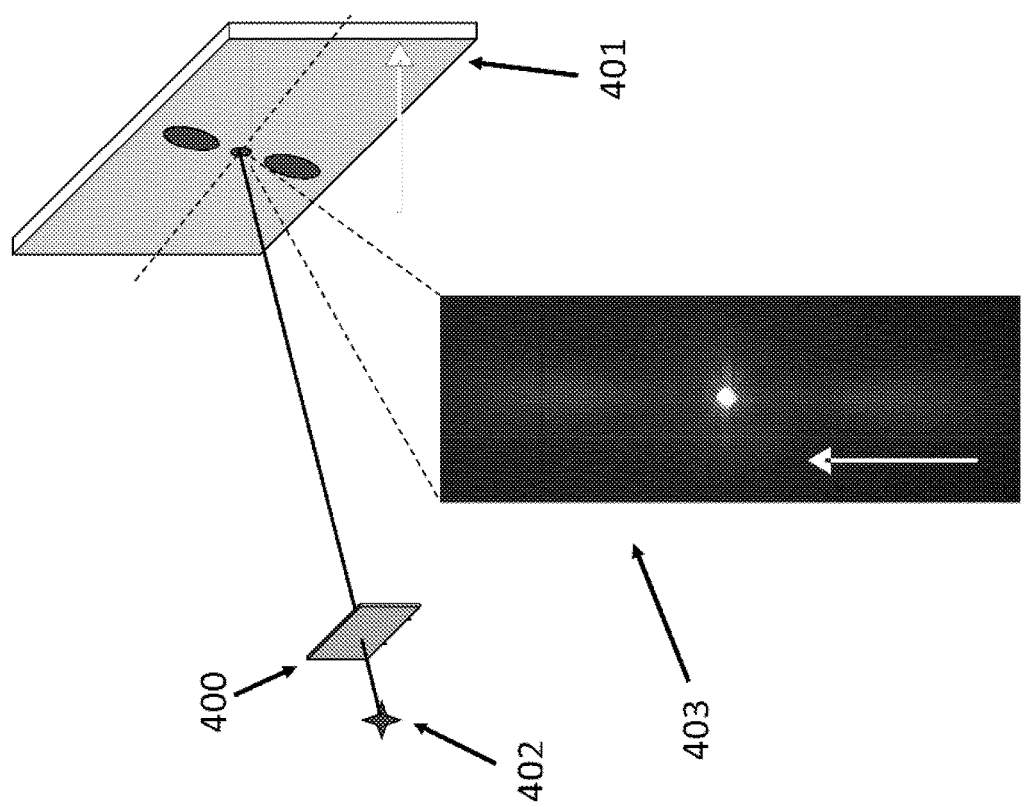
FIG. 9 presents the optical setup including sample 400 (aligned collagen membrane), screen 401 to project diffraction image 403, and laser source 402 with wavelength in the visible range. The diffraction pattern having two centrally symmetric "petals" elongated along the fibril alignment direction is typical for an aligned-crimped collagen membrane.

After delaminating the collagen membranes from a plastic substrate and converting them into thread-like constructs (scaffold) by rolling and folding at air-liquid interface as described further in, Biocomposites and method of making the same, U.S. patent application Ser. No. 12/539,563, (2009). their cross-sections were measured by SEM (FIG. 7). Here the membranes A and D have substantially tubular bodies with one lumen extending therethrough the thread-like construct. The thread-like construct B has multiple elongated cavities and the construct C has three lumens extending therethrough the thread. The thread-like graft two weeks after implantation into mammal subject is presented in FIG. 8. The picture is made by polarized optical microscope.

The foregoing methods, materials, constructs and description are intended to be illustrative. In view of the teachings provided herein, other approaches will be evident to those of skill in the relevant art, and such approaches are intended to fall within the scope of the present invention.

EXAMPLES

A number of experiments were carried out for illustration purposes. The following experiments are intended to describe and illustrate various embodiments in more detail, and are not intended to limit the disclosure in any way.

Example 1

Mammalian cell alignment on the collagen membrane with an aligned uniaxial or biaxial structure.

Figure 17:
FIG. 17 shows human skin fibroblasts grown on uniaxial collagen membrane align along the fibrils. Note the crimped pattern of the membrane.
Figure 18:
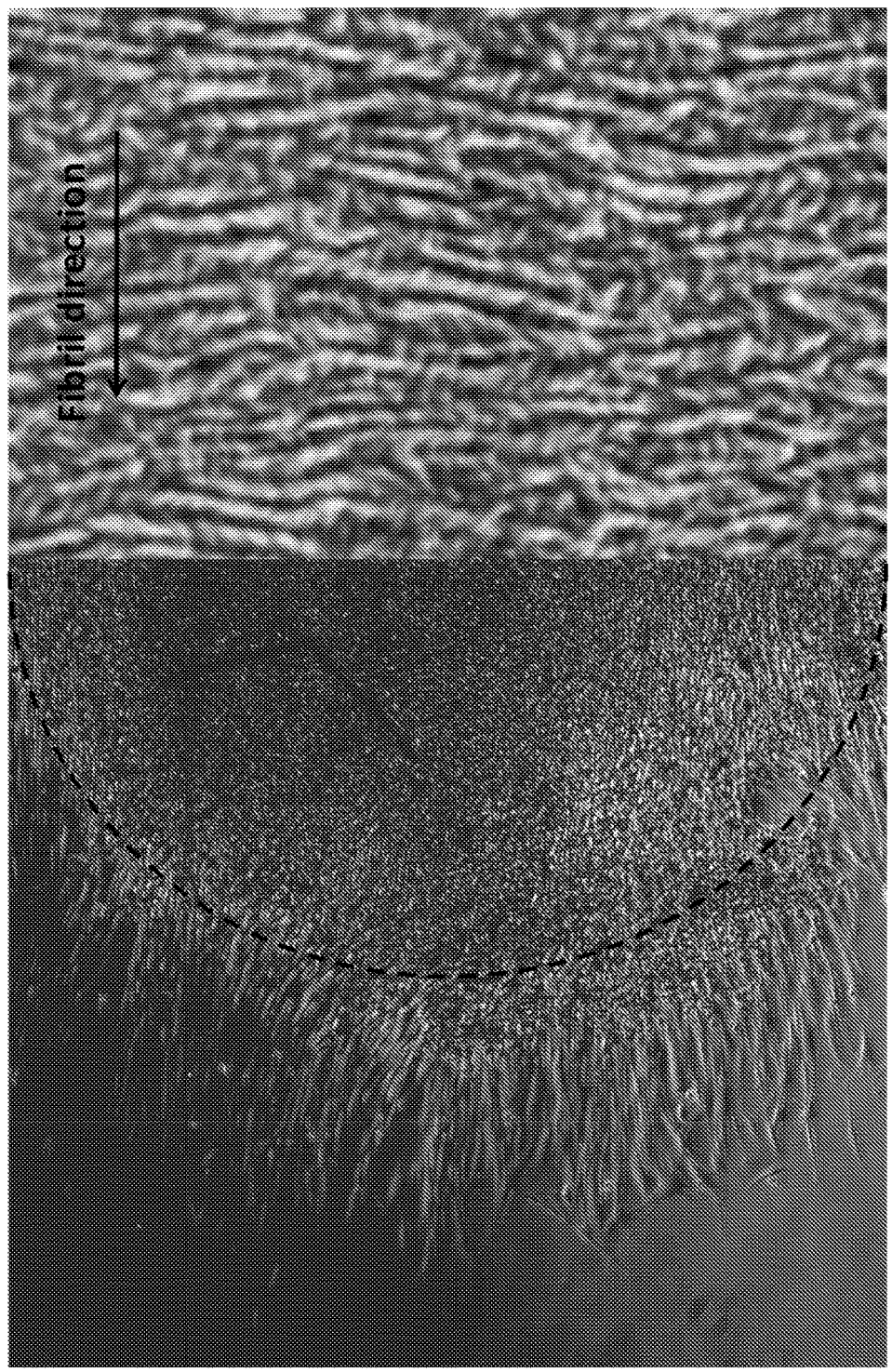
FIG. 18 shows human fibroblasts plated on aligned-crimped collagen membrane migrate mainly along the fibrils, not along the crimps or grooves.

Fibroblasts plated on the collagen membrane with an aligned uniaxial structure align substantially along the direction of the crimped fibrils (FIG. 17) and migrate along the fibrils, not along the crimps or grooves (FIG. 18).

Figure 19:
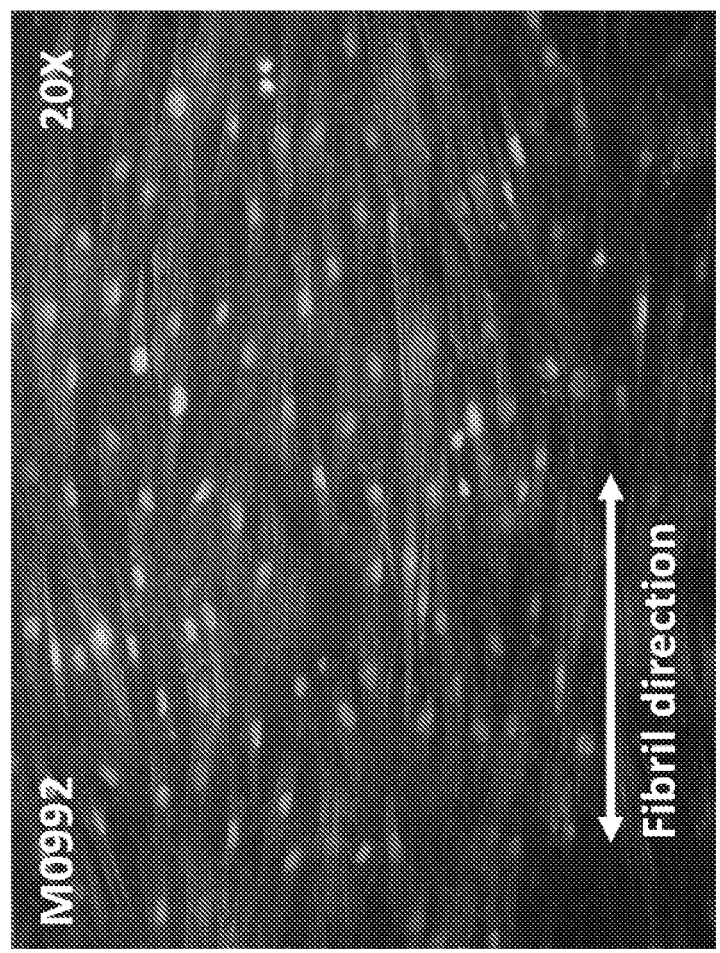
FIG. 19 shows human mesenchymal stem cells grown on uniaxial collagen membrane align along the fibrils; stained for cytoskeletal fibrillar actin and nuclei.

Mesenchymal stem cells plated on the collagen membrane with an aligned uniaxial structure align substantially along the direction of the crimped fibrils (FIG. 19).

Figure 20:
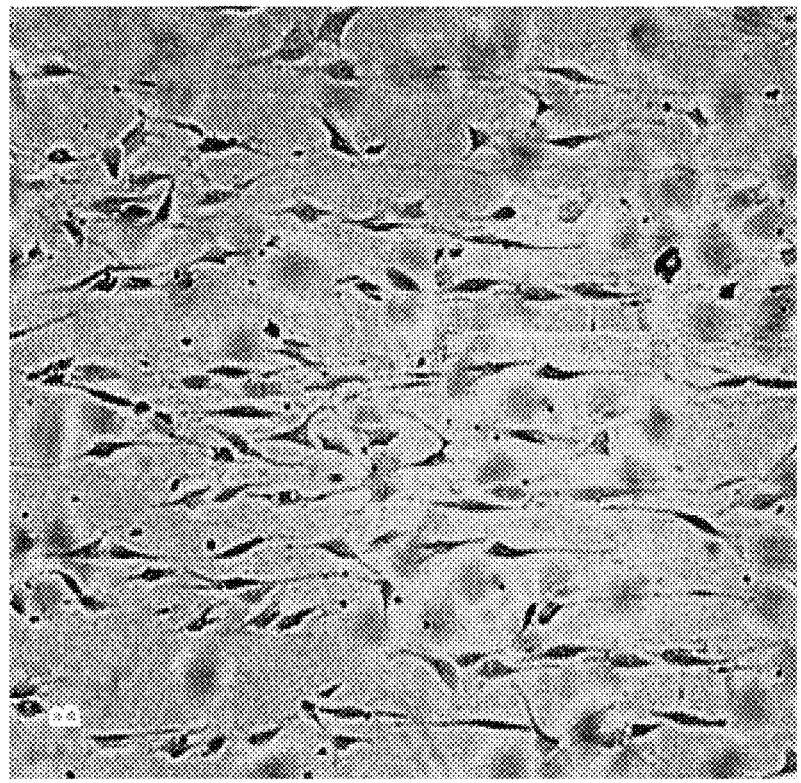
FIGS. 20A and 20B show epithelial cells (HaCat) grown on uniaxial collagen membrane align along the fibrils (right, FIG. 20B) as compared to conventional collagen coating (left, FIG. 20B).
Figure 20:
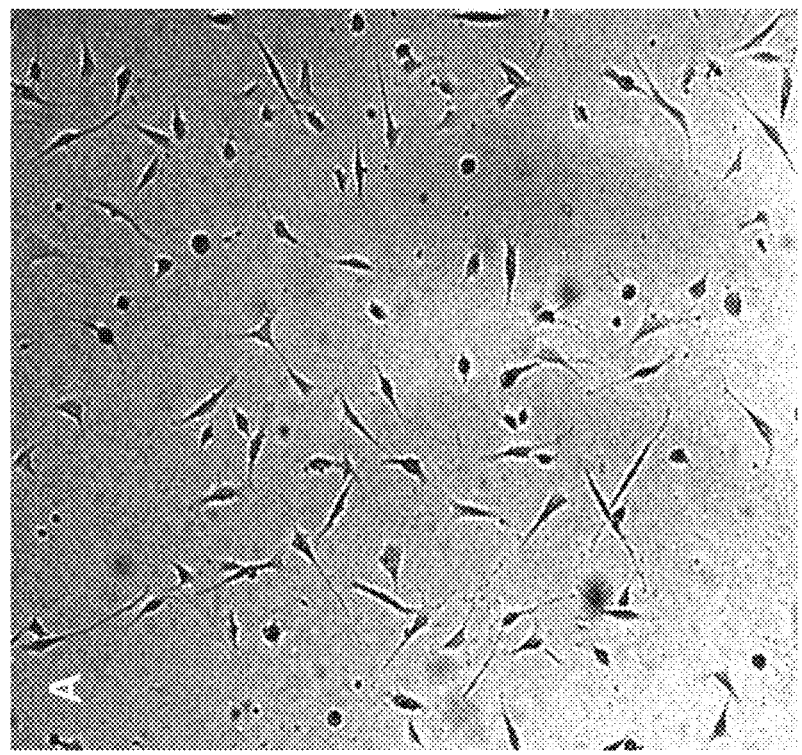

Epithelial cells plated on the collagen membrane with an aligned uniaxial structure align substantially along the direction of the crimped fibrils (FIG. 20).

Figure 21:
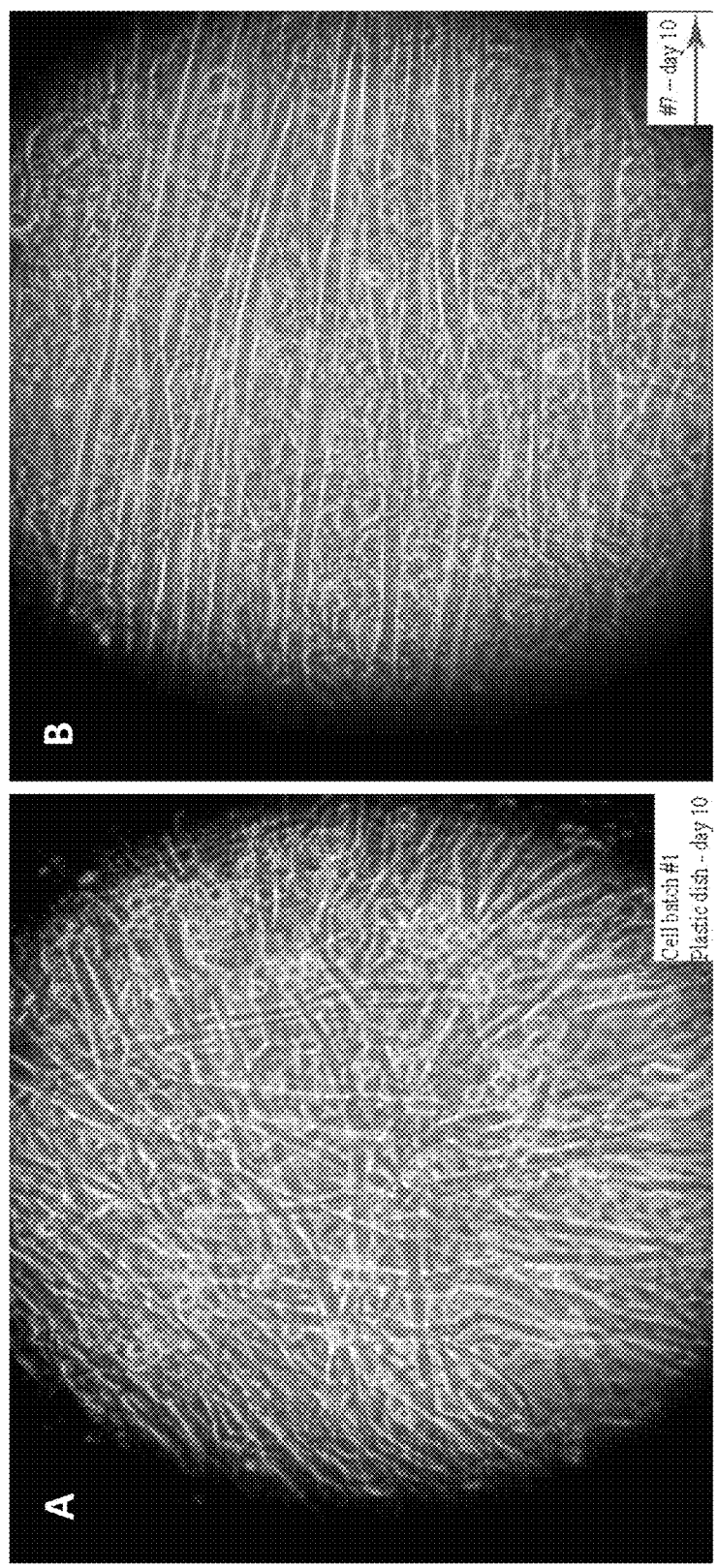
FIGS. 21A and 21B show myoblasts grown on uniaxial collagen membrane align and fuse into myotubes along the fibrils (right, FIG. 21B), as compared to myoblasts grown on tissue culture plastic (left, FIG. 21B), which form myotubes with random orientation.

Myoblasts plated on the collagen membrane with an aligned uniaxial structure align substantially along the direction of the crimped fibrils, resulting in myotube formation also aligned along the direction of the crimped fibrils (FIG. 21).

Figure 22:
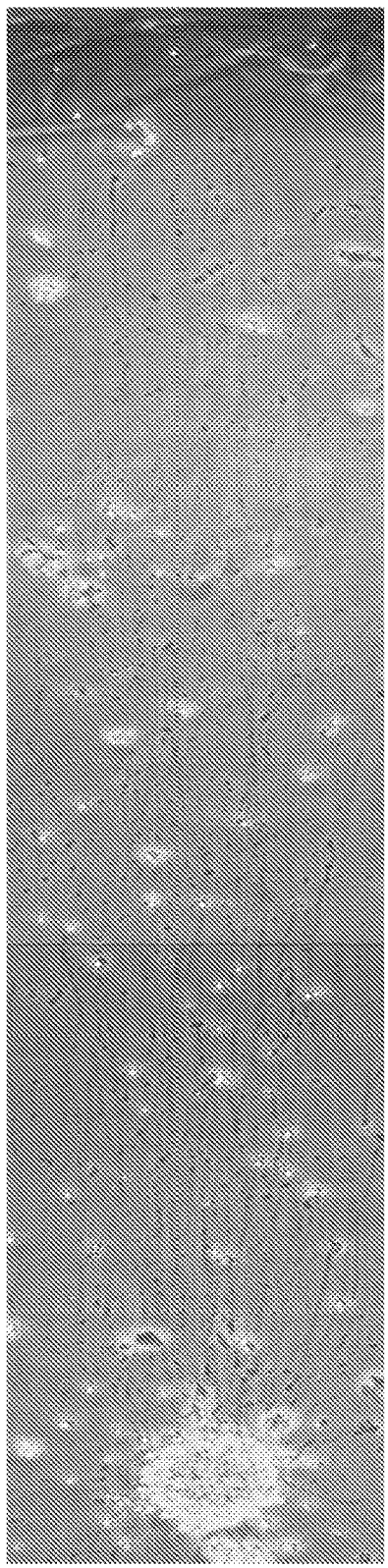
FIG. 22 shows rat primary cortical neurons (E18) grown on aligned-crimped collagen membrane extending neurites along the fibrils but perpendicular to the ridges and grooves.

Neurons plated on the collagen membrane with an aligned uniaxial structure extend neurites aligned substantially along the direction of the crimped fibrils (FIG. 22).

Figure 23:
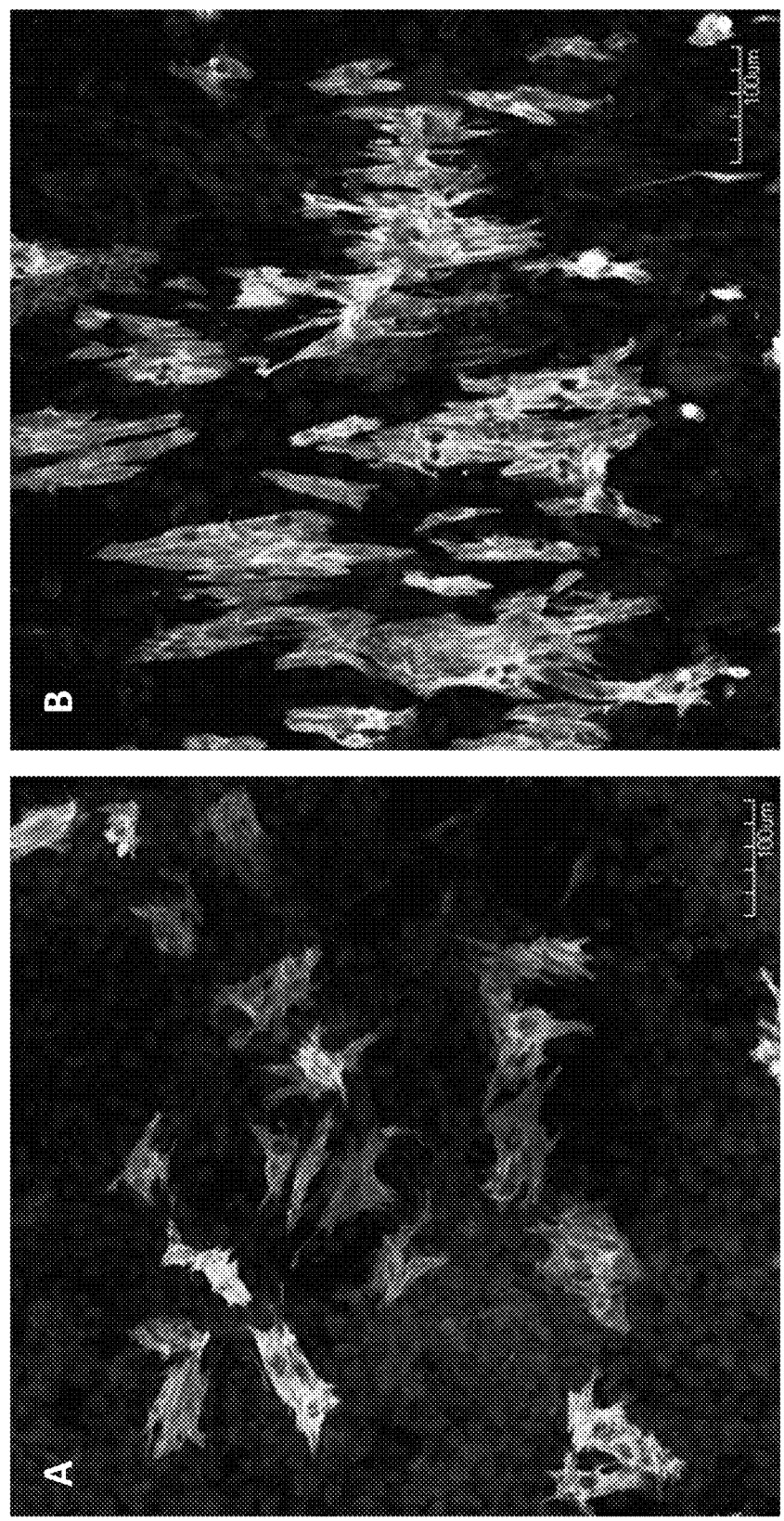
FIGS. 23A and 23B show cardiomyocytes differentiated from hESC on uniaxial collagen membrane, which align along the fibrils (right, FIG. 23B), unlike those on conventionally collagen-coated tissue culture plastic (left, FIG. 23A).

Cardiomyocytes differentiated from hESC plated on the collagen membrane with an aligned uniaxial structure align substantially along the direction of the crimped fibrils (FIG. 23).

Figure 24:
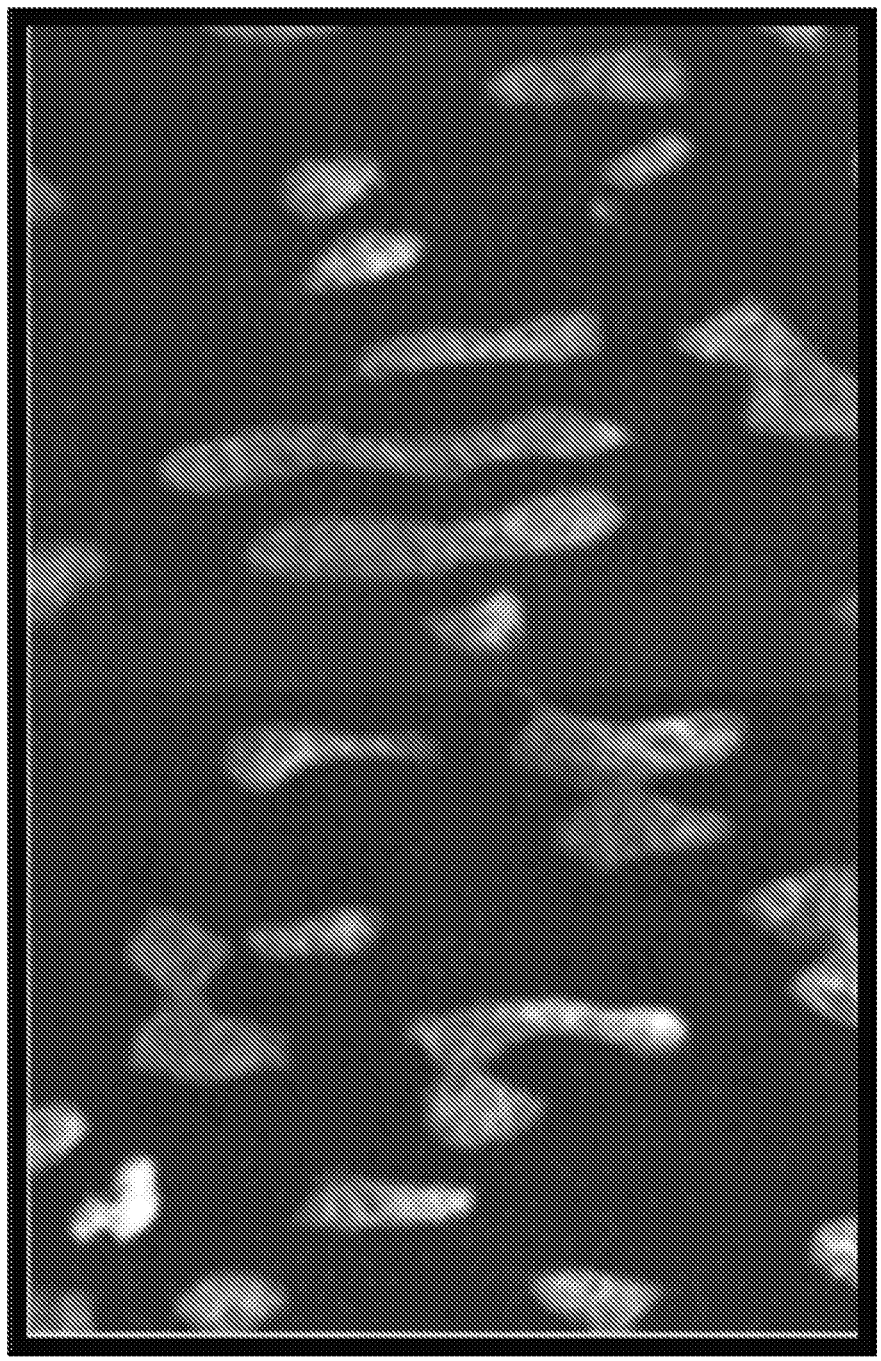
FIG. 24 shows MDCK cells grown on uniaxial collagen membrane form tubules aligned along the fibrils.

MDCK cells plated on the collagen membrane with an aligned uniaxial structure arrange into tubular structures which are aligned substantially along the direction of the crimped fibrils (FIG. 24).

Example 2

Examples of cross-linking of collagen membranes.

The collagen scaffolds can be crosslinked: by PEG with riboflavin as photoinitiator, see G Papavasiliou, P Songprawat, V, E Hammes, M Morris, et al., Three-Dimensional Patterning of Poly(Ethylene Glycol) Hydrogels Through Surface-Initiated Photopolymerization. *Tissue Eng Part C Methods.* 14(2):129-40 (2008) under UV irradiation (370 nm) for 10 min; by genipin (1% concentration of genipin, Wako Pure Chemical Industries, Ltd., Japan, in 70% EtOH at 20° C. for 3, 6, and 24 hours as described at Long Bi, Zheng Cao, Yunyu Hu, Yang Song, Long Yu, et al., Effects of different cross-linking conditions on the properties of genipin-cross-linked chitosan/collagen scaffolds for cartilage tissue engineering *J Mater Sci: Mater Med.* 22, 51-62 (2011).; by dehydrothermal (DHT) treatment see X. Cheng, U. A. Gurkan, C. J. Dehen, M. P. Tate, H. W. Hillhouse, et al., An electrochemical fabrication process for the assembly of anisotropically oriented collagen bundles, *Biomaterials* 29, (22), 3278-88 (2008) at 100° C. under 50 mtorr vacuum for 24, 48, and 72 h. Comparing the above crosslinking methods we concluded that the tread-like collagen scaffolds crosslinked by genipin provided the material with the highest resistance to degradation by collagenase, and showed possibility to control the rate of degradation by varying the time of the procedure.

Example 3

Viscoelastic properties of the thread-like construct.
Description of the Uniaxial Tension Tester.

The experimental setup for mechanical characterization consists of the transport stage with precision micrometer under control of Zaber T-LA28 linear actuator and digital force gauge M5-012 (Mark-10, Copiague, N.Y.). The actuator is driven by a stepper motor with speed range from 0.0022 mm/sec to 8 mm/sec, with accuracy of +/−8 um and repeatability better than 1 μm. The digital force gauge has resolution better than 0.1 g and loading limit about 80 g. A small environmental chamber is used to maintain high humidity around the moist thread during the test. The thread is suspended between the stationary force gauge and linear actuator above a small pool of liquid. A glass plate covers the top of the chamber and allows observation with the reflective microscope during test. A 2 mm high slot at each end of the chamber clears the thread by 1 mm on each side so that it is clear of any station at surfaces. The slots are narrow enough to minimize airflow exchange during the short test of approximately 5 minutes. Both, digital force gauge and linear actuator are independently controlled by computer. To measure the viscoelastic properties of the thread we torn on the digital force gauge setting to measure the "start threshold" at 1 gram then we turn on the linear actuator such that the actual force acquisition starts when the force exceeds 1 gram. The typical length of the tested scaffold was 30 mm, the wet length was 20 mm, and dry cross-section was 1×25000 μm.

Results of Tensile Testing.

Figure 10:
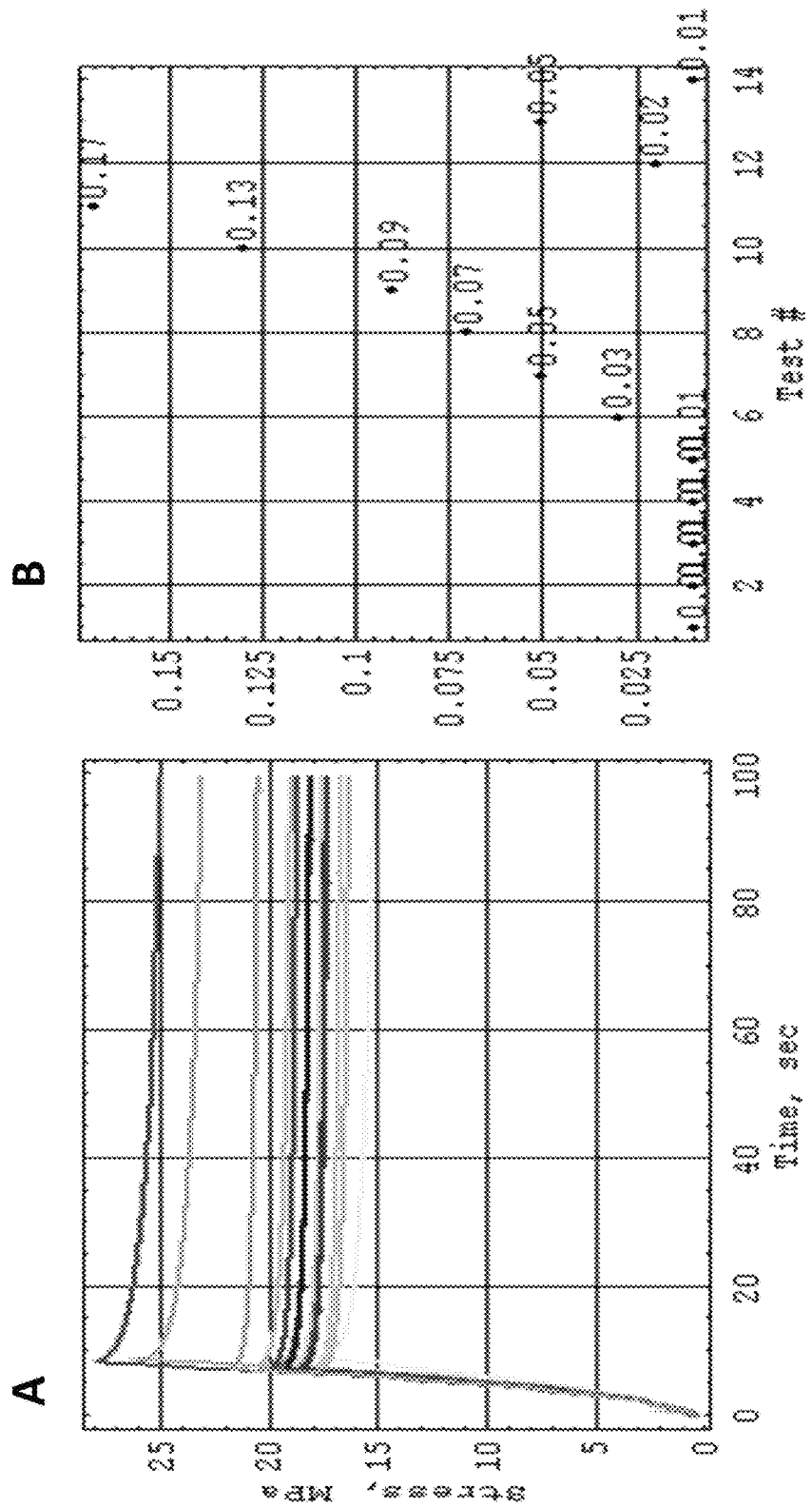
FIGS. 10A and 10B show results of viscoelastic measurements of the thread-like construct (scaffold) cross-linked by genipin for 3 hours (left) for the sequence of deformation speeds in mm/sec (right).

The typical results of uniaxial measurements for thread-like construct (graft) crosslinked by genipin in wet conditions are presented in FIG. 10. Analysis of the measurements reveals the fundamental nature of viscoelastic characteristics of the nanoweave collagen threads. We found that after a few initial measurements which cause the hardening of the thread material (precondition to a load pattern), further tensile loading measurements are very repeatable, at least within the tested speed interval. Thus, these measurements can be approximated by the formula:

$$f(t,v) - f(0) = C_1(-1 + e^{C_2 t}) = C_1\left(-1 + e^{C_2 \frac{x}{v}}\right) \quad (1)$$

where f=f(t, v) be a measured force, t—time, x—displacement, v—the speed of the deformation, C1 and C2 are the constants, and f(0)=v) is the constant close to the "start threshold". In terms of stress-strain coordinates the last equation can be easily transform into the form $$\sigma(\varepsilon,v) = A(-1 + e^{B*\varepsilon}) \quad (2)$$

which is the typical expression to describe the nonlinear concave elastic response that is characteristic of many soft tissues (tendon, ligaments, blood vessels, etc), see e.g. S D Abramowitch, S L Woo, An improved method to analyze the stress relaxation of ligaments following a finite ramp time based on the quasi-linear viscoelastic theory, *J. Biomech. Eng.* 126, 92-97 (2004); and the definitions of soft tissue as defined in the art, for example at http://en.wikipedia.org/wiki/Soft_tissue Thus the construct (graft) has Fung-elastic material properties after precondition to a load pattern. The approximation (2) has been tested for our thread-like constructs (scaffolds) for the speed of deformation v ranging from 0.01 mm/sec to 1 mm/sec. Of course, each thread-like scaffold has slightly different parameters (constants) A and B. The typical constants for the 3 hour genipin cross-linked construct (scaffold) are: A=1.53; B=5.25. The constants are very little changed with the speed of deformation. Each curve in the FIG. 10 has two branches. The first one going to the maximum stress corresponds to the constant speed of deformation and can be represented by the approximation (2). The second branch is the relaxation curve which corresponds to the cessation (v=0) at some time point. The sequence of the curves from bottom to top (FIG. 10, left) corresponds to the sequence of experiments (FIG. 10, right). The last four experimental curves have the same slope. The first curve (v=0.01 mm/sec) has a little different slope.

The measured tensile strength (wet state) for the 3 hour genipin crosslinked constructs (scaffolds) is 25.8±0.89 MPa and for 6 hour genipin crosslinked constructs (scaffolds) is 27.97±1.56 MPa. The 3 hour genipin crosslinked scaffolds and 6 hour genipin crosslinked scaffolds have statistically insignificant difference in rigidity (A and B constants). The values of the constants A and B measured in a wet state for different types of cross-linking and for different speeds of loadings change within the following ranges: 0.2 MPa<A<300 MPa; 0.5 MPa<B<200 MPa.

Figure 11:
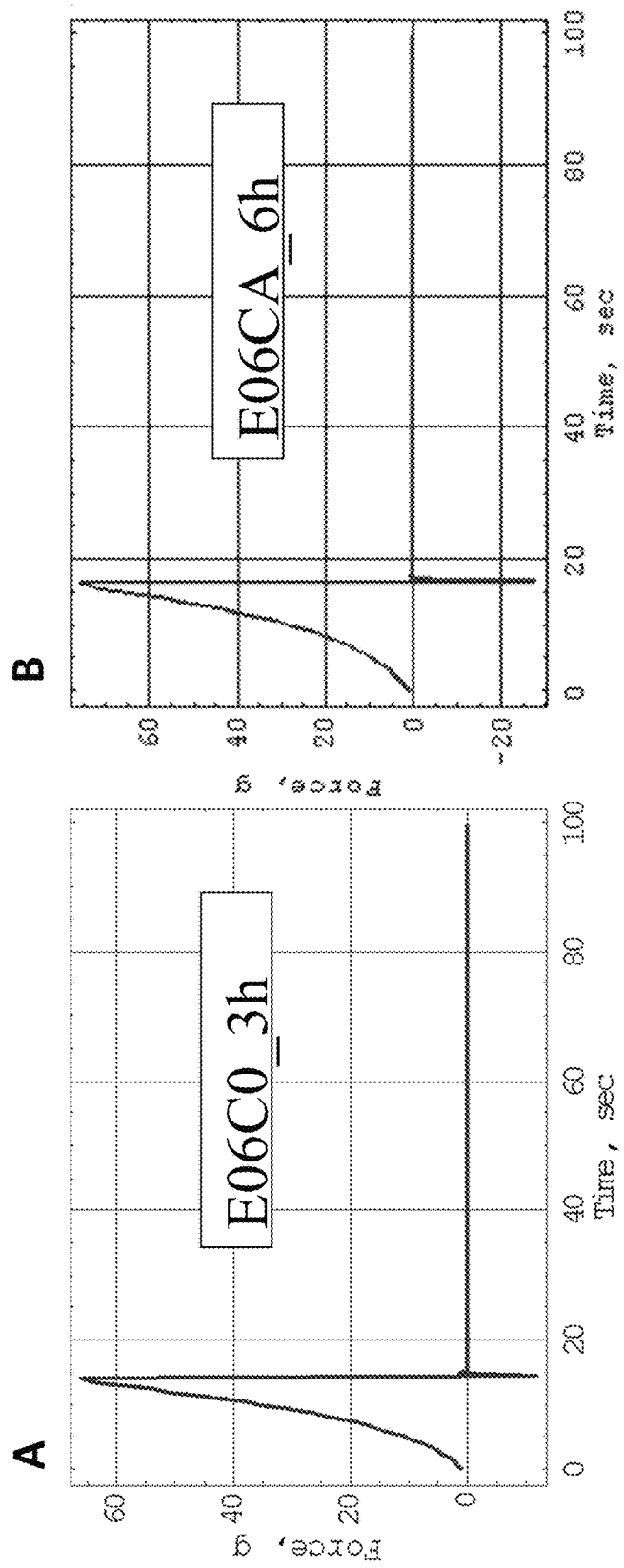
FIGS. 11A and 11B show uniaxial tensile tests for constant speed of deformation of 0.03 mm/sec for two thread-like collagen constructs (fibrils are aligned along to the construct length). The first one (E06C0_3h) is crosslinked by genipin for 3 hours; the second one (E06C0_6h) is crosslinked by genipin for 6 hours.

The typical "break curves" are shown in FIG. 11. Thus, our thread-like scaffolds have the mechanical properties similar to a soft tissue, as defined in the art, such as for example as described at18. http://en.wikipedia.org/wiki/Soft_tissue.

Example A: Collagen Membrane Having an Aligned-Crimped Structure Guides Endothelial Cell Alignment Primary human dermal microvascular endothelial cells (ECs) and human induced pluripotent stem cell-derived-ECs (iPSC-ECs) were cultured in EGM2-MV (Lonza) growth medium. For in vitro studies, aligned-crimped collagen membranes and scaffolds were sterilized in 70% ethanol and then rinsed in phosphate-buffered saline (PBS) before cell seeding at $1.3 \times 10^4$ cells/cm$^2$ for 7 days (n≥3). As a control substrate that does not contain ordered nanofibrillar collagen (random collagen), we coated glass substrates with 0.35 mg/mL collagen I (BD Biosciences) for cell culture.

Figure 27:
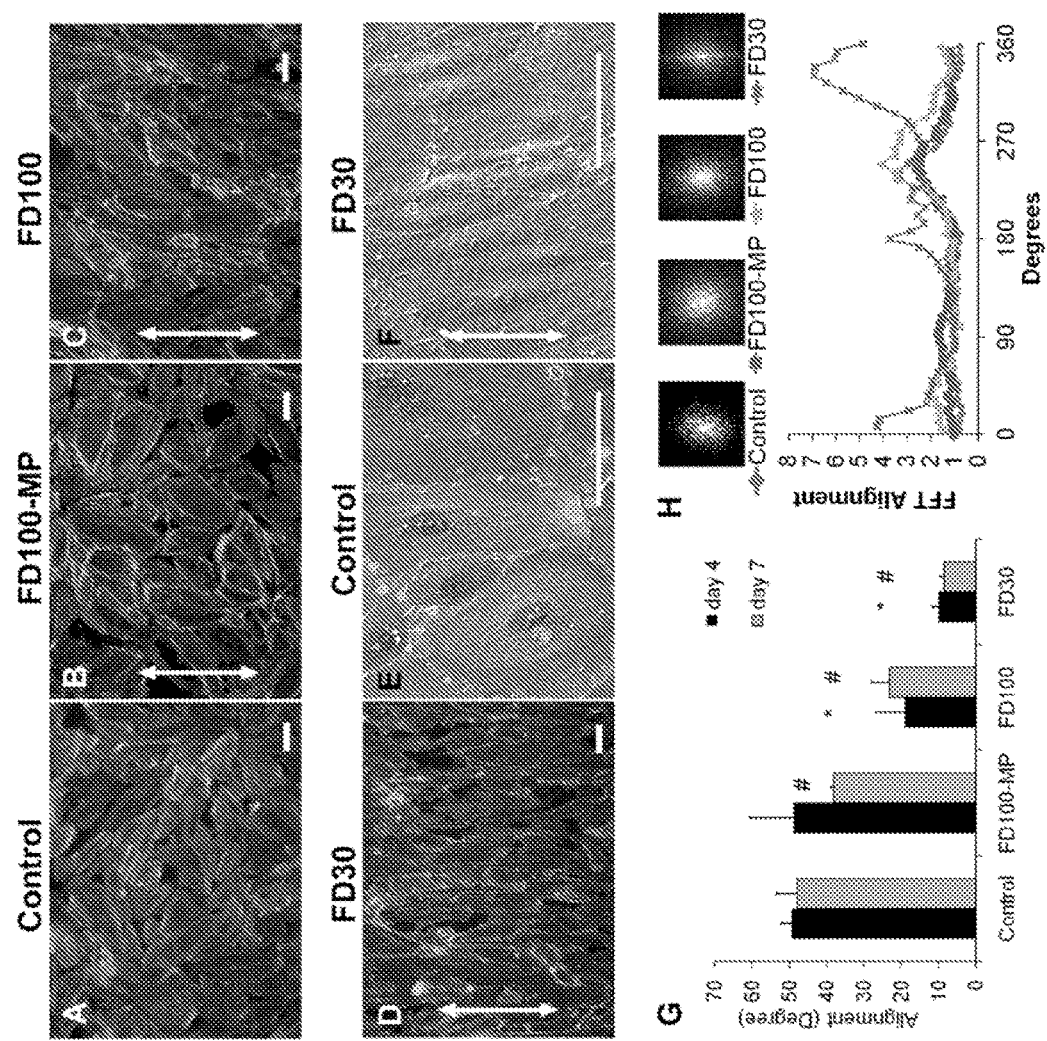
FIGS. 27A-27H show endothelial cell (EC) morphology on aligned-crimped nanofibrillar membranes. Immunofluorescence staining with phalloidin for cytoskeletal protein F-actin and Hoechst for nuclei after 7 days of cell culture on (FIG. 27A) random collagen coating (control)

Nanofibrils having diameters of less than 100 nm diameters (FD100) should be used since we did not observe alignment of ECs grown on these substrates. Preferably, fibrils with diameters smaller than 100 nm diameter are used, and in some examples a diameter of 30 nm (FD30) is used, with the hypothesis that ECs may sense and respond to smaller architectural elements. To examine the effect of nanotopographical features on cytoskeletal assembly, we fluorescently stained for cytoskeletal F-actin fibers using phalloidin. Fluorescence microscopy revealed dramatic effects on cellular orientation induced by these modified substrates (FIG. 27A-D). After 4 days of cell seeding, ECs on FD30 and FD100 substrates had significantly organized F-actin assembly that were 9±2° or 19±8° along the nanofibril direction, respectively, whereas cells cultured on the control substrates had F-actin fibers randomly distributed within 49±3° with respect to an arbitrary axis (p<0.0001, FIG. 27G; in this analysis, a value of 45° represents entirely random orientation of axis of cultured cells). The addition of microgrooves appeared to reverse the effect of 100-nm fibrils on cell guidance, as samples on the FD100-MP samples were not significantly different from the control substrates on day 4. After 7 days when the cells were confluent, cells on FD30 and FD100 substrates remained significantly aligned, in comparison to the control substrate (9±2° FD30 vs 23±5° FD100 vs 48±6° control, p<0.0001, FIG. 27G). The cells on FD30 were notably elongated in morphology, in comparison to the ECs on the control substrates which had larger cell area and "cobble-stone" morphology, as shown by SEM (FIG. 27E-F).

As an additional method for quantification of F-actin assembly, we used automated two-dimensional Fast Fourier Transform (FFT) analysis to generate frequency plots and alignment histograms. The frequency plots depict random orientation as pixels evenly distributed about the origin, and parallel alignment as pixels organized along the axis of the nanofibrils. In this analysis, the frequency plots depict distinct organization of pixels along the fiber axis on the FD30 samples (FIG. 27H inset), whereas the control substrates are represented by pixels evenly distributed about the origin. The frequency plots were also displayed as frequency alignment histograms that depict the principal angle of orientation within 360° of space (FIG. 27H). Based on FFT analysis, the alignment on control substrates consists of low frequency peaks with a Gaussian distribution that is commonly observed in randomly oriented assemblies. In contrast, the alignment histograms for the FD30 substrate showed 2 distinctive peaks separated by 180°, suggesting that the cells primarily align along the same direction. Therefore, the FFT analysis (FIG. 27H) concurs with cellular alignment analysis (FIG. 27G) that FD30 substrates promote EC alignment along the direction of collagen nanofibrils.

Figure 28:
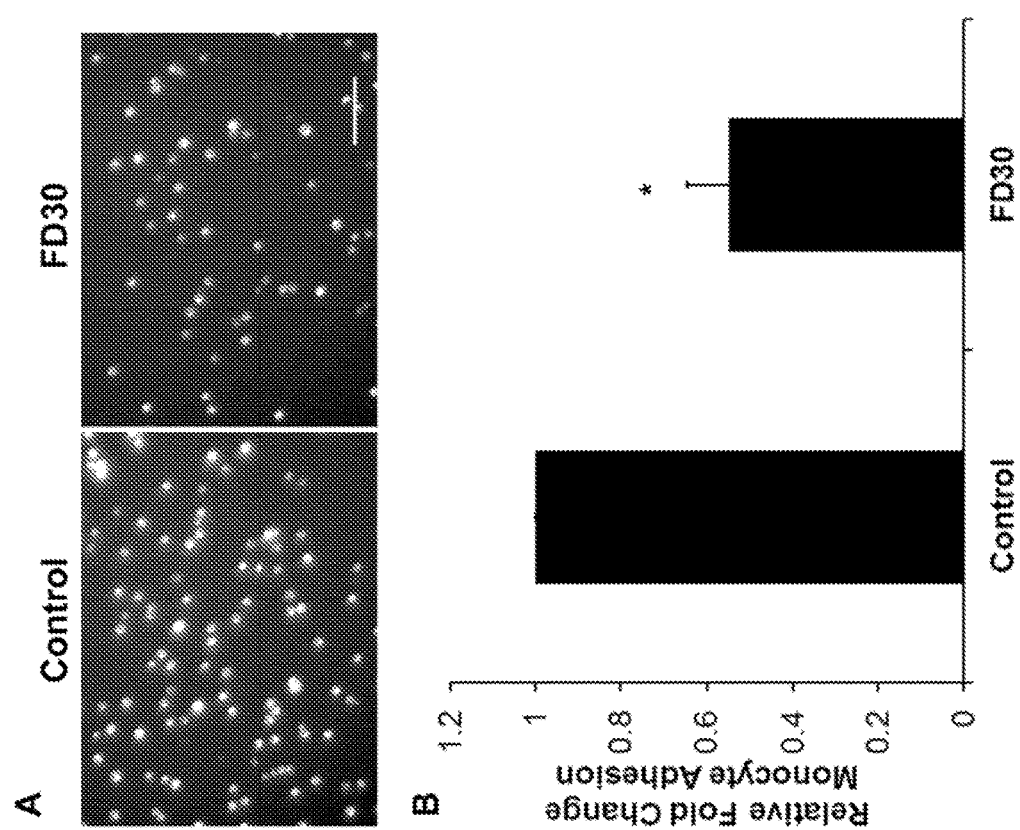
FIGS. 28A-28B compare monocyte adhesion onto monolayer of ECs (endothelial cells) plated on aligned-crimped collagen membrane (FD30) vs. monolayer of ECs plated on random collagen coating.

Example B: Aligned-Crimped Collagen Membrane Modulates Endothelial Inflammatory Properties It is well established that laminar shear stress modulates both endothelial function and morphology. ECs exposed to laminar blood flow in a straight segment of an artery are aligned longitudinally along the direction of blood flow, and aligned ECs are less adhesive for monocyte attachment as described in Cooke J P. Flow, no, and atherogenesis. Proc. Natl. Acad. Sci. U.S.A. 2003; 100:768-770. To determine if nanofibril-induced cellular alignment could also confer similar functional effects, we cultured ECs on either the FD30 or control substrates to confluency. ECs that were aligned on FD30 substrates or non-aligned on the control substrates were then exposed to the inflammatory cytokine, TNFα, followed by the incubation of the ECs with fluorescently labeled monocytes. Notably, for the ECs grown on FD30 collagen, there was a 50% reduction in the numbers of adherent monocytes by comparison to the ECs grown on random collagen. This observation suggests that, even in the absence of shear stress, nanofibril-induced EC alignment could modulate their functional ability to resist monocyte adhesion (FIG. 28).

Example C: Aligned-Crimped Nanofibrillar Collagen Scaffolds Improve EC Survival Upon Subcutaneous Implantation and Implantation into the Ischemic Hindlimb In addition to evaluating endothelial morphology and function in vitro, we assessed whether aligned FD30 nanofibrillar collagen membranes could enhance the survival of implanted ECs under physiological or pathophysiological conditions. Human ECs in an aligned flow field have enhanced survival by comparison to those in a disturbed flow field. For example, ECs in the disturbed flow field at the iliac artery bifurcation manifest shorter telomeres, an indication of more frequent cell turnover in these zones [30] Chang E, Harley C B. Telomere length and replicative aging in human vascular tissues. Proc. Natl. Acad. Sci. U.S.A. 1995; 92:11190-11194. Accordingly, in addition to evaluating endothelial morphology and function in vitro, we assessed whether aligned FD30 nanofibrillar collagen scaffolds could enhance the survival of implanted ECs under physiological or pathophysiological conditions. The nanofibrillar FD30 membranes were rolled and folded into three-dimensional thread-like multi-luminal scaffolds, crosslinked by DNT for 72 h, and then characterized for mechanical properties. Uniaxial tension tests for the collagen scaffold with cross-section 1.2 µm×25000 µm (~180 µm effective diameter) showed that its maximum load was 2.1 N in dry state, 0.9 N in wet state, and its elastic modulus was 160±20 MPa. These mechanical properties are consistent with collagen materials with high mechanical strength.

Figure 29:
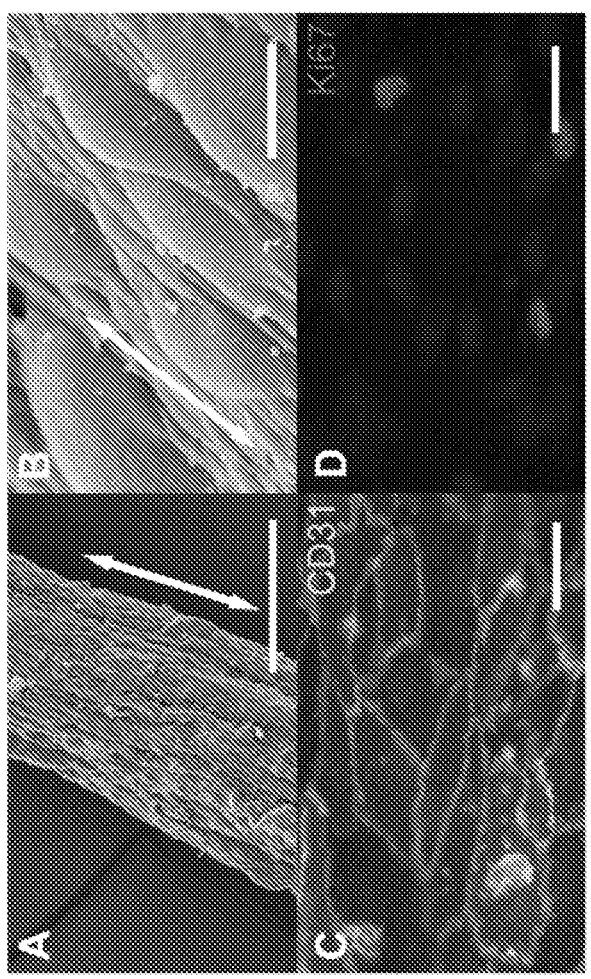
FIGS. 29A-29D show endothelial morphology and phenotype on FD30 collagen scaffolds. A-B) SEM of FD30 scaffolds at low (FIG. 29A) and high magnification (FIG. 29B).

We cultured ECs on FD30 nanofibrillar scaffolds. Based on SEM microscopy, the ECs were generally aligned longitudinally along the direction of the nanofibrils (FIG. 29A-B). The ECs maintained robust expression of the endothelial specific marker CD31 (FIG. 29C) and proliferation antigen Ki67 (FIG. 29D), suggesting that the cells maintained their phenotype and proliferated on the scaffold.

Each scaffold contained ~4000 cells, as quantified by dissociation of the cells from the graft after confluent cell attachment.

We investigated the ability of aligned nanofibrillar scaffolds as cell delivery vehicles to maintain cell viability upon transplantation. To enable non-invasive imaging of the transplanted ECs by BLI and fluorescence microscopy, we genetically modified the cells with a lentiviral construct and purified the cells that were transduced based on GFP expression.

Figure 30:
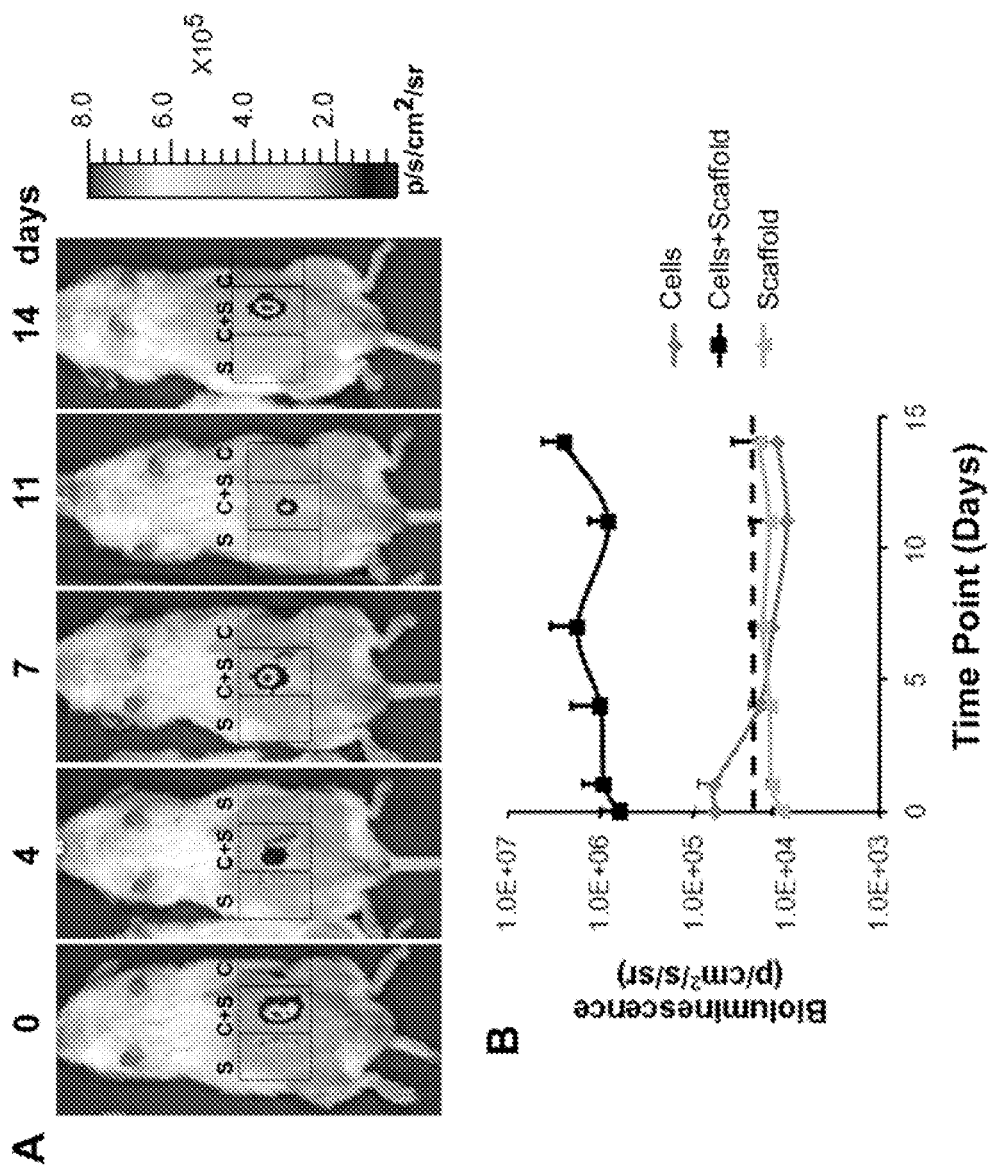
FIGS. 30A-30B show Aligned-crimped nanofibrillar collagen graft enhances endothelial survival after subcutaneous implantation.

To examine the effect of aligned-crimped nanofibrillar collagen on EC survival, male NOD SCID (13-16 weeks old) mice received subcutaneous abdominal transplants of FD30 collagen scaffold, $4 \times 10^3$ ECs in DMEM, or $4 \times 10^3$ ECs cultured on the FD30 scaffold (n=4). Using BLI to track cell survival and localization in subcutaneous implants, we demonstrated that the EC-seeded scaffolds showed prolonged survival for at least 14 days, with an average in bioluminescence intensity of $6.2 \pm 0.4 \times 10^5$ ps$^{-1}$ cm$^{-2}$ sr$^{-1}$ on day 0 and $2.4 \pm 1.9 \times 10^6$ ps$^{-1}$ cm$^{-2}$ sr$^{-1}$ on day 14 (FIG. 30). In stark contrast, when similar numbers of cells were injected in media in the absence of the scaffold, the average bioluminescence intensity was 10-fold lower at $5.7 \pm 4.0 \times 10^4$ ps$^{-1}$ cm$^{-2}$ sr$^{-1}$ on day 0, which was significantly lower than that of the cell-seeded graft group (p<0.03), and by day 4 the group treated with cells in media no longer had a signal above threshold. The discrepancy in bioluminescence signal on day 0 between the cell-containing groups is consistent with greater spreading of transplanted cells in the saline formulation to the interstitial space and more rapid clearance. The acellular scaffold group demonstrated no detectable signal besides for endogenous background that was below threshold. These data indicated that the human ECs delivered subcutaneously were no longer viable or were cleared from the region of implantation within 4 days. By contrast, when the cells were delivered on the nanofibrillar scaffold, the cells remained viable and localized to the transplant site for at least 14 days.

Figure 31:
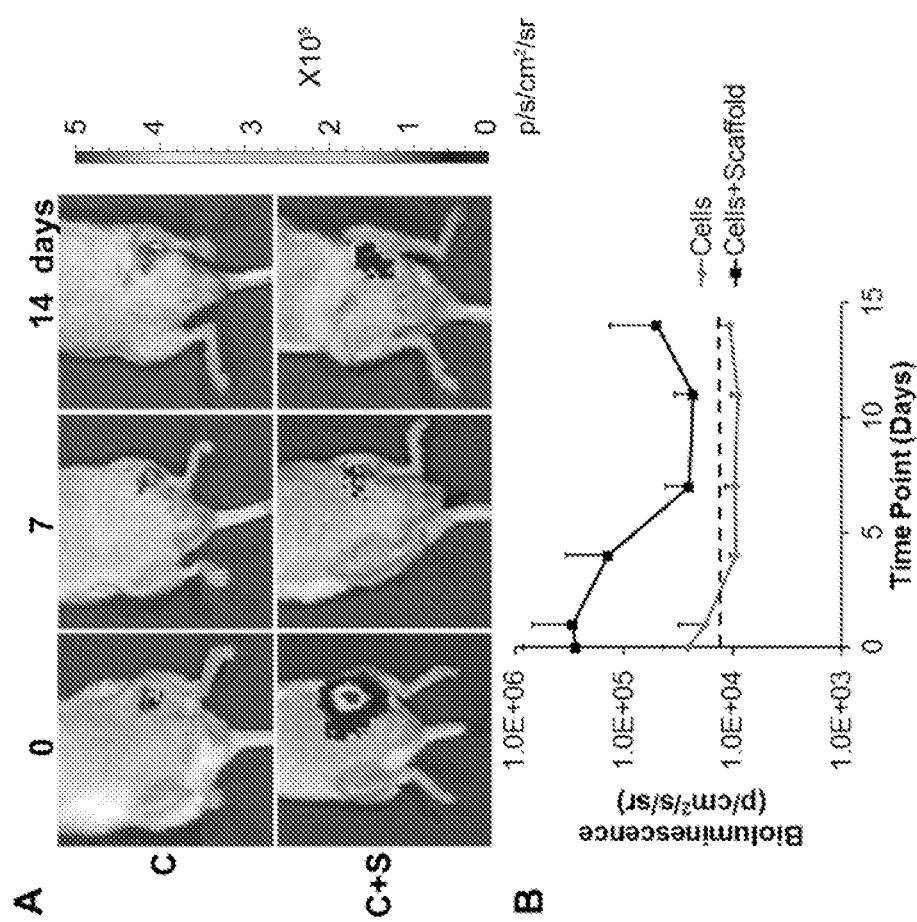
FIGS. 31A and 31B illustrate Aligned-crimped nanofibrillar collagen graft enhances endothelial survival after implantation into ischemic hindlimb.

Based on the finding of enhanced EC cell survival in non-diseased subcutaneous tissue, we next examined whether aligned FD30 nanofibrillar scaffolds could also maintain cell survival in the hostile environment of an ischemic tissue, where death of implanted cells is increased due to hypoxia, inflammation, and reduced nutrient availability. Upon induction of hindlimb ischemia by excision of the femoral artery, we transplanted $4 \times 10^3$ ECs in saline or cultured on the FD30 scaffolds in the bed of the excised femoral artery. Notably, the cells on scaffolds survived for up to 14 days, although there was gradual decrease in bioluminescence intensity from day 0 ($2.8 \pm 0.6 \times 10^5$ ps$^{-1}$ cm$^{-2}$ sr$^{-1}$) to day 14 ($5.1 \pm 0.9 \times 10^4$ ps$^{-1}$ cm$^{-2}$ sr$^{-1}$) (FIG. 31). In stark contrast, the cells delivered in saline underwent rapid decrease in signal from $2.6 \pm 1.8 \times 10^4$ ps$^{-1}$ cm$^{-2}$ sr$^{-1}$ on day 0 to undetectable levels by day 4.

Figure 25:
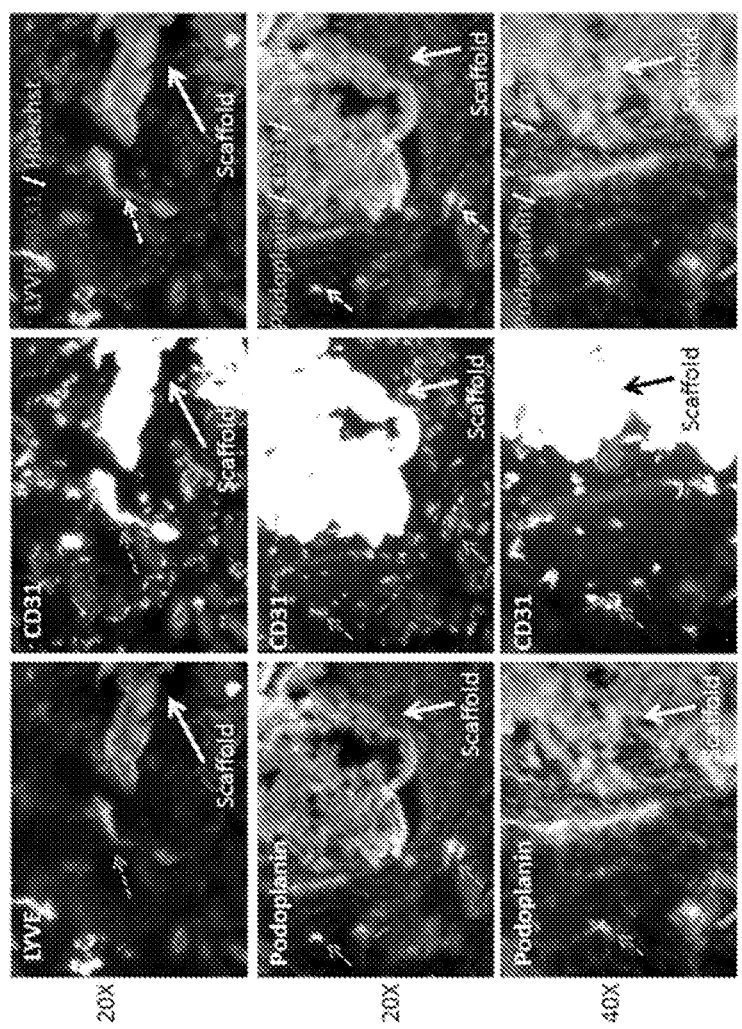
FIG. 25 shows histological analysis of vascular regeneration after subcutaneous implantation of genipin-crosslinked collagen graft (thread-like construct) for 14 days. Immunofluorescence staining demonstrates the formation of endogenous lymphatic vessels that co-express lymphatic markers LYVE1 and podoplanin, in addition to general endothelial marker CD31. The collagen graft autofluoresces in both fluorescence emission wavelengths recorded. Solid arrows point to collagen graft, and dotted arrows point to vascular structures.

Example D: The Construct Promotes Angiogenesis, Directed Vascular and Lymphatic Regeneration Human primary lymphatic endothelial cells were seeded onto a thread-like construct manufactured from aligned uniaxial collagen scaffold with 30-nm fibril diameter (scaffold). It is estimated that about $3 \times 10^4 - 5 \times 10^4$ cells attach to the scaffolds. Three days after seeding the cells onto the scaffolds, the scaffolds were transplanted subcutaneously into SCID mice (n=4 per group). To determine whether the collagen scaffold attracts vessel formation, we performed histological analysis of the scaffolds at 14 days post implantation. The subcutaneous space around the scaffold included blood endothelial cells and lymphatic endothelial cells, as demonstrated by immunofluorescence staining of transverse sections (FIG. 25). We observed the presence of endogenous murine blood vessels, based on the expression of the general endothelial marker, CD31. A subset of the blood vessels colocalized with lymphatic markers podoplanin and LYVE1. These data demonstrate that lymphatic and blood vessels are recruited to the region near the collagen scaffold after 14 days.

Figure 26:
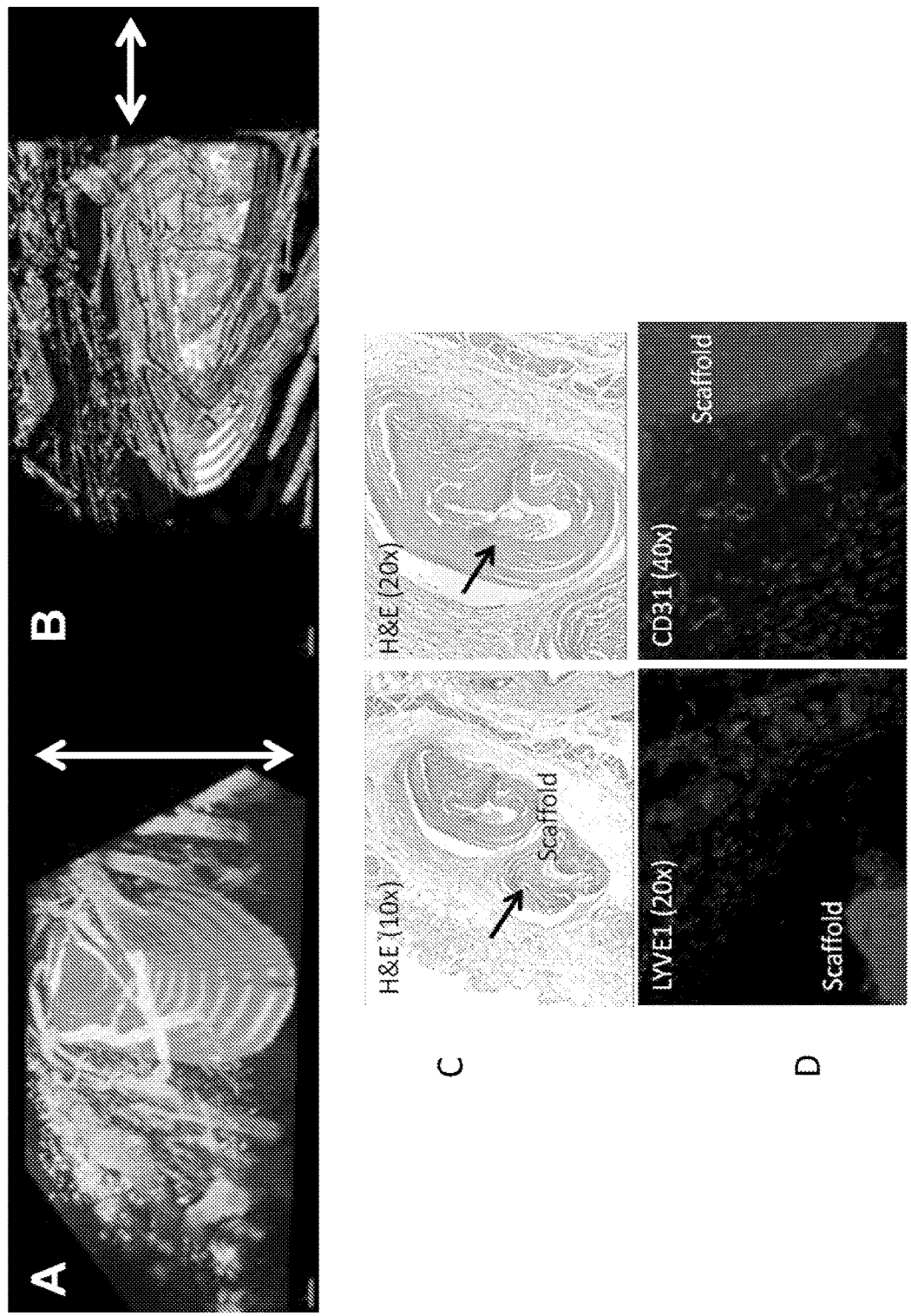
FIG. 26 D shows Immunofluorescence staining of vessels for murine LYVE1 and CD31, in close proximity to the graft. The collagen graft shows substantial autofluorescence.

To further examine whether these vessels are functionally perfused, we performed additional studies in which the collagen scaffolds were implanted for 5 weeks for intravital and histological analysis. Intravital imaging of functional vessels was performed by systemically injecting fluorescently labeled dextran as a reporter dye. After 1 h, the animals were imaged by intravital two-photon microscopy to reveal fluorescently labeled vessels. As shown in FIG. 26, abundant vessels surrounded the scaffold as shown by the light-colored vessels. Many of these vessels were aligned along the direction of the nanofibrils, which is denoted by the direction of the arrow. These results suggest that abundant vessels are recruited to the surroundings of the nanopatterned scaffold.

To reveal the identity of the vessels, we histologically stained cross-sections of the grafts with murine-specific antibodies. As shown by the H&E staining of the scaffold (graft) in FIG. 26C, the multiluminal structure of the collagen scaffold was observed. The scaffold appeared to be infiltrated by cells both within as well surrounding its external boundary. Within close vicinity of the scaffold, there were endogenous lymphatic blood vessels that expressed LYVE1, as well as blood vessels that expressed CD31 but not LYVE1.

Example E

Bilayer collagen membrane with the top layer having an aligned-crimped structure and the bottom layer having aligned-crimped structure such that the alignment directions of the top and bottom layers forming the 90° angle where the mammalian cells plated on the membrane align substantially perpendicular to the ridges and grooves of the crimp pattern and substantially along the direction of the crimped fibrils (endothelial cells (EC) on the top and smooth muscle cells (SMC) on the bottom).

Figure 12:
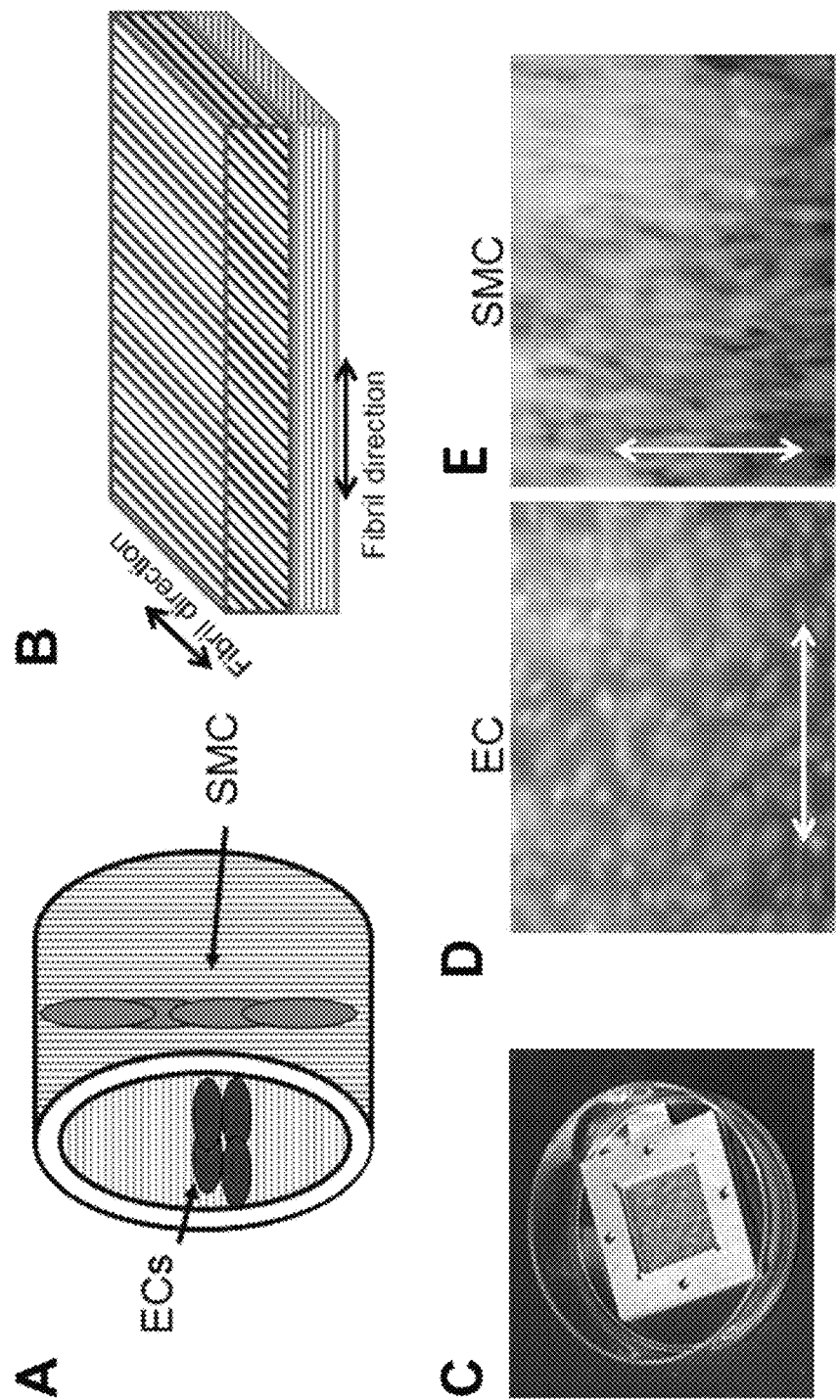
FIGS. 12A-12E show a series of photographs and drawings illustrating the use of a multilayer collagen graft with orthogonal orientation of fibrils. Two different cell types are plated on the top and bottom sides of the construct (e.g., epithelial and endothelial cells in the case of corneal model and smooth muscle and endothelial cells in the case of the blood vessel model). The graft with the attached cells can be further transferred to a specific site in the body for therapeutic purposes.
Figure 13:
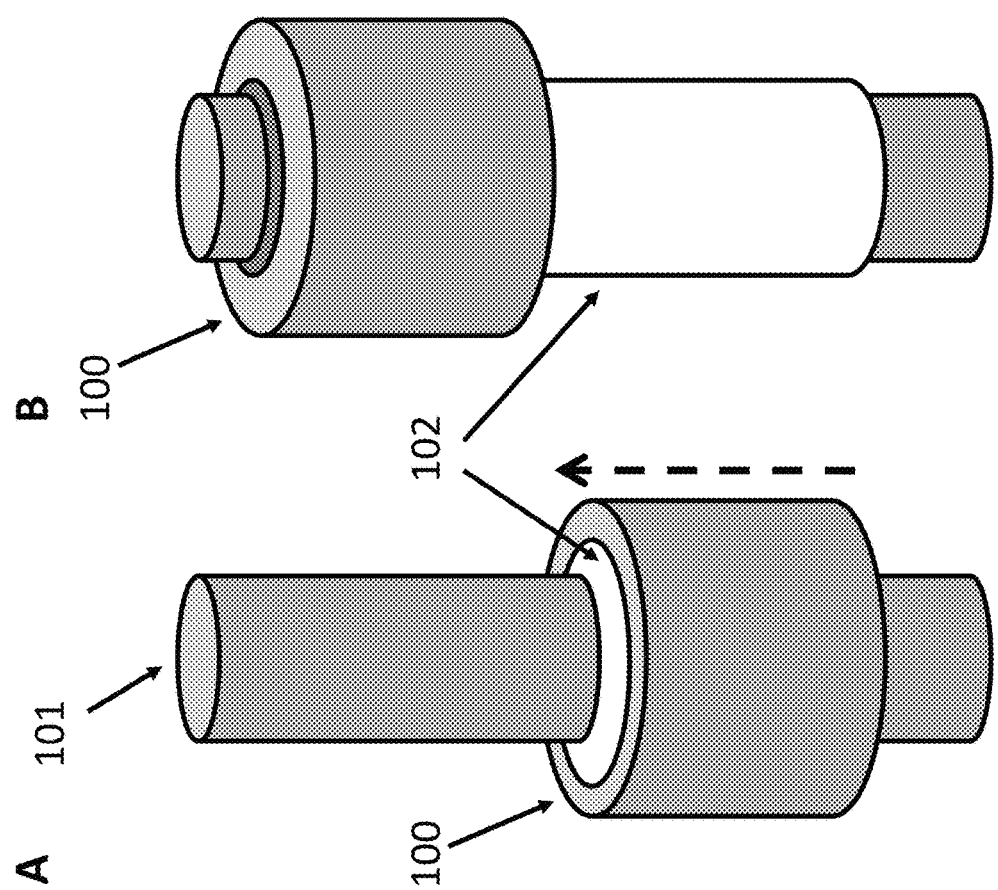
FIGS. 13A and 13B show a schematic drawing of the coating process. There are shown two positions of the coating head 100 which deposits collagen 102 to the thin plastic film (e.g., PET) tightly covering the cylindrical shaft 101. Temperature sensitive surface can be used instead of PCT. This coating device is similar to one described in the U.S. patent application Ser. No. 11/951,324 but adopted for cylindrical geometry. A similar coating process can be used to deposit several layers of collagen and/or other biopolymers directly to the external or internal surface of a tubular implant. The dried cylindrical aligned collagen membrane can be further removed from the plastic film. Several coating layers can be made by this process. The alignment direction is defined by the coating head movement which can be rotational and vertical.

To mimic the orthogonal alignment of cells between the intimal and medial layers (FIG. 12A), we constructed bilayered membranes consisting of an aligned-crimped top membrane with 30 nm fibril diameter to guide the assembly of ECs and an aligned-crimped top membrane with 100 nm fibril diameter for SMC culture. The nanofibrils of the two membranes were oriented orthogonal to one another to mimic their physiological orientation (FIG. 12B). As shown in FIG. 12C, the bilayered membranes were secured in metal frames for sequential seeding of ECs and then SMCs. After 3 days of culture, we visualized cell viability and alignment using calcein AM fluorescent dye. FIG. 12D demonstrates the orthogonal alignment of ECs and SMCs that match their orthogonal alignment in vivo. This data suggests that nanotopographical cues may be beneficial for guiding cellular alignment and function in engineered vascular conduits.

Example F

Autologous lymph node or lymph node fragment or mammal decellularized lymph node can be placed into a carrier and attached (sutured) to thread-like construct for minimally invasive delivery into a mammal subject by catheter, trocar, or other minimally invasive procedure, wherein the construct promotes survival of the lymph node and integration of the lymph node into a lymphatic network in the mammalian subject, at the site of transfer or transplantation. A nodular compartment (300) shown in the FIG. 16A can be used as a carrier for lymph node or lymph node fragment or mammal decellularized lymph node. The lymph node can be supplemented by VEGF-C growth factor, see the patent application [28] 28. Alitalo K. et al. Autologous lymph node transfer in combination with VEGF-C or VEGF-D growth factor therapy to treat secondary lymphedema and to improve reconstitutive surgery. 2012. US 2012/0125348 A1 and the references there.

What is claimed is:

1. A graft comprising: a collagen membrane comprised of crimped collagen fibrils such that the membrane has an aligned uniaxial or biaxial structure and more than 50% of mammalian fibroblasts plated on the membrane align parallel to the direction of the collagen fibrils, wherein the membrane guides endothelial cell assembly parallel to the alignment direction which diminishes adherence of monocytes in comparison with adherence to endothelial cells plated on a membrane with random fibril orientation.

2. A graft according to claim 1, where the graft further comprises a collagen membrane having an aligned-crimped structure which exhibit a crimp pattern, such that more than 50% of mammalian fibroblasts plated on the membrane align perpendicular to ridges and grooves of the crimp pattern and parallel to the direction of the crimped fibrils.

3. A graft according to claim 1, wherein the membrane has a transmission diffraction pattern produced by a laser source with wavelength in the visible range, such that the pattern has at least two centrally symmetric elongated "petals".

4. A graft according to claim 1, wherein more than 50% of the collagen fibrils have a diameter in the range from 20 nm to 60 nm.

5. A graft according to claim 1, wherein the membrane is rolled and folded in a thread-like construct such that an alignment direction of the membrane is oriented along the thread-like construct, wherein the construct is further cross-linked and has viscoelastic properties under uniaxial load.

6. A graft according to claim 5, wherein the thread-like construct has at least one cavity elongated substantially along the construct suitable for carrying cells, growth factors, drugs, other suitable bioactive materials and cell formations like endothelial spheroids and islets.

7. A graft according to claim 6, wherein the cells are selected from the group consisting of myocyte precursor cells, smooth muscle cells, cardiac myocytes, skeletal myocytes, satellite cells, fibroblasts, cardiac fibroblasts, chondrocytes, osteoblasts, osteocytes, endothelial cells, epithelial cells, epidermal cells, embryonic stem cells, hemopoietic cells, neuronal cells, Schwann cells, mesenchymal stem cells, glial cells, dorsal root ganglia, anchorage-dependent cell precursors, or combinations thereof.

8. A graft according to claim 5, wherein the thread-like construct has a multi-luminal nodular compartment suitable for embedding thymus derived stromal cells and bone marrow derived dendritic cells to generate a lymph node-like immune response function, and the flanking thread-like sections with no or single lumen suitable to carry and align endothelial cells to integrate the lymph node prosthesis into lymphatic system and link it to the blood circulation.

9. A graft according to claim 5, wherein the thread-like construct has multi-luminal structure with crimped fibrils align along its length and multiple lumens within the construct running parallel with the construct length, but start and stop at various places along the construct.

10. A graft according to claim 5, wherein the construct has diameter ranges from 50 μm to 2 mm in a dry state and tensile strength is higher than 0.2 MPa in the wet state.

11. A graft according to claim 5, wherein the construct has Fung-elastic material properties after precondition to a load pattern with the constant A ranging from 0.2 MPa to 300 MPa and constant B ranging from 0.5 MPa to 200 MPa when measured in the wet state.

12. A graft according to claim 5, wherein the construct promotes angiogenesis, vascularization and serves as means for guiding migration and orientation of endothelial cells along the alignment direction, as well as the cell localization.

13. A graft according to claim 5 comprising a substantially tubular body, wherein the body has an exterior surface, an interior surface, and at least one lumen extending therethrough such that a fluid flow through the lumen can direct endothelial cell migration.

14. A graft according to claim 5 or 13, wherein the construct promotes directed vascular or lymphatic regeneration along the alignment direction.

15. A graft according to claim 13, wherein the exterior surface has aligned-crimped structure and the interior surface has aligned-crimped structure such that the alignment directions of the exterior and interior surfaces form non-zero angle.

16. A graft according to claim 15, wherein the angle is the 90° angle and the alignment direction of the crimped fibrils of the interior surface coincides with the direction of at least one lumen.

17. A graft according to claim 1 or 5, wherein the membrane guides endothelial cell assembly along the alignment direction and extends the survival of cells in ischemic tissue.

18. A graft according to claim 1 or 5, wherein the membrane is formed of at least one or more type of collagens: I, II, III, IV, V, VI or XI.

19. A graft according to claim 5, wherein at least one thread-like construct is attached to a carrier with lymph node or lymph node fragment or mammalian decellularized lymph node and prepared for transferring or transplanting a graft in a mammalian subject by catheter, trocar, or other minimally invasive procedure, wherein the construct promotes survival of the lymph node and integration of the lymph node into a lymphatic network in the mammalian subject, at the site of transfer or transplantation.

20. A graft comprising: a multilayer collagen membrane with a top layer having collagen fibrils in an aligned-crimped structure and a bottom layer having collagen fibrils in an aligned-crimped structure such that the alignment directions of the top and bottom layers form an angle, wherein more than 50% of the mammalian cells that are plated on the membrane align perpendicular to ridges and grooves of the crimp pattern and parallel to the direction of the crimped fibrils in each layer, wherein the cells are selected from the group consisting of myocyte, smooth muscle cells, cardiac myocytes, fibroblasts, endothelial cells, neuronal cells, mesenchymal stem cells, or combinations thereof and wherein at least one membrane is comprised of more than 50% of collagen fibrils with diameter in range from 20 nm to 60 nm.

21. The graft according to claim 1, 5 or 20, wherein it further comprises growth factors, peptides, elastin, fibrin, heparin, proteoglycans, glycoproteins, hyaluronan, cross-linking agents, or combinations thereof.

* * * * *